(12) United States Patent
Fisker

(10) Patent No.: US 10,327,873 B2
(45) Date of Patent: Jun. 25, 2019

(54) METHOD, SYSTEM AND USER INTERFACE FOR CREATING A DIGITAL DESIGN FOR USE IN MANUFACTURING A MOLDING-SHELL FOR A DENTAL RESTORATION

(71) Applicant: 3SHAPE A/S, Copenhagen K (DK)

(72) Inventor: Rune Fisker, Virum (DK)

(73) Assignee: 3Shape A/S, Copenhagen K (DK)

( * ) Notice: Subject to any disclaimer, the term of this patent is extended or adjusted under 35 U.S.C. 154(b) by 127 days.

(21) Appl. No.: 15/521,934

(22) PCT Filed: Oct. 23, 2015

(86) PCT No.: PCT/EP2015/074645
§ 371 (c)(1),
(2) Date: Apr. 26, 2017

(87) PCT Pub. No.: WO2016/066552
PCT Pub. Date: May 6, 2016

(65) Prior Publication Data
US 2017/0312058 A1 Nov. 2, 2017

(30) Foreign Application Priority Data

Oct. 27, 2014 (DK) .................................. 201470655

(51) Int. Cl.
*G06F 19/00* (2018.01)
*A61C 13/00* (2006.01)
(Continued)

(52) U.S. Cl.
CPC ............ *A61C 13/0004* (2013.01); *A61C 5/77* (2017.02); *A61C 9/0046* (2013.01); *A61C 13/20* (2013.01); *A61C 13/0001* (2013.01)

(58) Field of Classification Search
CPC ..... A61C 13/0004; A61C 9/0046; A61C 5/77; A61C 13/20; A61C 13/0001
See application file for complete search history.

(56) References Cited

U.S. PATENT DOCUMENTS 4,411,626 A 10/1983 Becker et al.
4,742,464 A 5/1988 Duret et al.
(Continued)

FOREIGN PATENT DOCUMENTS

| WO | WO 00/32131 A1 | 6/2000 | |
|---|---|---|---|
| WO | WO-2013079437 A2 * | 6/2013 | ......... A61C 13/0004 |
| WO | WO 2014/053549 A1 | 4/2014 | |

OTHER PUBLICATIONS

International Search Report (PCT/ISA/210) dated Jan. 29, 2016, by the European Patent Office as the International Searching Authority for International Application No. PCT/EP2015/074645.
(Continued)

*Primary Examiner* — Michael D Masinick
(74) *Attorney, Agent, or Firm* — Buchanan Ingersoll & Rooney PC

(57) ABSTRACT

A method, a system and a user interface for generating a digital design for use in the manufacture of a molding-shell for a patient's teeth, where the molding-shell and the teeth together enclose a volume for forming a dental restoration, include obtaining a digital 3D representation of the patient's teeth, the digital 3D representation including a tooth part relating to one or more teeth for which the dental restoration is formed; obtaining a set of one or more digital teeth anatomies; arranging the set of digital teeth anatomies and the digital 3D representation according to a preferred relative arrangement; and generating the digital design where a first portion of the digital design is derived from the digital (Continued)

teeth anatomies and a second portion of the digital design is derived from the tooth part of the digital 3D representation.

25 Claims, 15 Drawing Sheets

(51) Int. Cl.
*A61C 13/20* (2006.01)
*A61C 5/77* (2017.01)
*A61C 9/00* (2006.01)
A61C 13/107 (2006.01)

(56) References Cited

U.S. PATENT DOCUMENTS

| | | | |
|---|---|---|---|
| 4,863,382 A * | 9/1989 | Bookstaber | A61C 13/273 433/172 |
| 7,059,850 B1 | 6/2006 | Phan et al. | |
| 2004/0137408 A1 | 7/2004 | Embert et al. | |
| 2004/0204787 A1 | 10/2004 | Kopelman et al. | |
| 2004/0209218 A1 | 10/2004 | Chishti et al. | |
| 2005/0042569 A1 | 2/2005 | Phan et al. | |
| 2006/0122719 A1 | 6/2006 | Kopelman et al. | |
| 2008/0153069 A1 | 6/2008 | Holzner et al. | |
| 2009/0248184 A1 | 10/2009 | Steingart et al. | |
| 2010/0015572 A1 | 1/2010 | Dierkes et al. | |
| 2012/0065756 A1 * | 3/2012 | Rubbert | A61O 5/007 700/98 |
| 2012/0139142 A1 | 6/2012 | Van Der Zel | |
| 2012/0175802 A1 | 7/2012 | Goetzinger et al. | |
| 2013/0006380 A1 | 1/2013 | Seiler | |
| 2013/0209961 A1 * | 8/2013 | Rubbert | A61K 6/0044 433/175 |
| 2013/0288202 A1 * | 10/2013 | Hochman | A61C 8/008 433/175 |

OTHER PUBLICATIONS

Written Opinion (PCT/ISA/237) dated Jan. 29, 2016, by the European Patent Office as the International Searching Authority for International Application No. PCT/EP2015/074645.

International Preliminary Report on Patentability (PCT/IPEA/409) dated Feb. 2, 2017, by the European Patent Office as the International Preliminary Examining Authority for International Application No. PCT/EP2015/074645.

Office Action (Communication) dated Oct. 19, 2018, by the European Patent Office in corresponding European Patent Application No. 15784404.4. (7 pages).

* cited by examiner

111

```
┌─────────────────────────────────────┐
│  Detect a line of contact between the│
│  digital 3D representation and the   │    112
│  digital teeth anatomies             │
└─────────────────────────────────────┘
                  │
                  ▼
┌─────────────────────────────────────┐
│  Deriving the first portion of the   │    113
│  digital design from the digital     │
│  teeth anatomies                     │
└─────────────────────────────────────┘
                  │
                  ▼
┌─────────────────────────────────────┐
│  Deriving the second portion of the  │    114
│  digital design from the digital 3D  │
│  representation                      │
└─────────────────────────────────────┘
                  │
                  ▼
┌─────────────────────────────────────┐
│  Creating an inner shell surface of  │
│  the digital design from the derived │    115
│  first and second portions           │
└─────────────────────────────────────┘
                  │
                  ▼
┌─────────────────────────────────────┐
│  Forming an outer shell surface of   │    116
│  the digital design                  │
└─────────────────────────────────────┘
                  │
                  ▼
┌─ ─ ─ ─ ─ ─ ─ ─ ─ ─ ─ ─ ─ ─ ─ ─ ─ ─ ┐
│  Add one or more support structures  │    117
│  to the digital molding-shell design │
└─ ─ ─ ─ ─ ─ ─ ─ ─ ─ ─ ─ ─ ─ ─ ─ ─ ─ ┘
                  │
                  ▼
┌─ ─ ─ ─ ─ ─ ─ ─ ─ ─ ─ ─ ─ ─ ─ ─ ─ ─ ┐
│  Define a channel in the digital     │    118
│  molding-shell design                │
└─ ─ ─ ─ ─ ─ ─ ─ ─ ─ ─ ─ ─ ─ ─ ─ ─ ─ ┘
```

*Fig. 1C*

METHOD, SYSTEM AND USER INTERFACE FOR CREATING A DIGITAL DESIGN FOR USE IN MANUFACTURING A MOLDING-SHELL FOR A DENTAL RESTORATION

TECHNICAL FIELD

This disclosure generally relates to a digital design for use in the manufacture of a molding-shell for forming a dental restoration for a patient's teeth, where the molding-shell and the teeth together enclose a volume for the dental restoration.

BACKGROUND

A dental restoration may for various reasons be designed and manufactured for a patient's teeth. This dental restoration may e.g. provide that the size, shape and/or shade of the restored teeth is modified compared to the size, shape and/or shade of the existing teeth. This is e.g. the case when the height of the teeth has been reduced due to e.g. grinding the teeth in sleep (Sleep Bruxism), when a portion of a tooth is damaged, or when the patient wishes to improve the aesthetic appearance of his teeth.

When a tooth is damaged, such as when a portion of the tooth is broken off, the extent of the damage may be so that a crown restoration is required for the tooth. The damaged tooth is then prepared for the crown restoration by grinding away tooth material making space for the crown restoration. The prepared tooth is often referred to as a tooth stump since its size is significantly less than that of the unprepared tooth. However, in other cases the dentist may decide that the remaining portion of the tooth is sufficiently healthy such that there is no need for preparing the tooth to form a tooth stump ready for accepting a crown restoration. Still the broken off portion may be large enough to cause significant irritation. In such cases the dentist often decides to manufacture a dental restoration, such as a crown restoration, which is seated in the existing damaged tooth where the dental restoration preferably is designed to provide that the shape of the restored tooth is anatomically correct and does not cause irritation.

When a patient has worn his teeth down to an extent where the patient's normal occlusion is disrupted, the result may be that the patient begins to experience problems in his temporomandibular joint (TMJ). Such problems may be solved by seating a table-top restoration on the worn teeth, where the table-top restoration is shaped such that the occlusal surface and hence the bite of the restored teeth is raised and a correct movement of the TMJ is restored. The table-top restoration preferably has one or more teeth restorations covering at least the occlusal surface of the worn teeth, especially the occlusal surface of posterior teeth which has a large impact on TMJ problems. However the table-top restoration does not necessarily cover the entire labial/buccal and lingual surfaces of the patient's teeth.

CAD/CAM technology is frequently used in the manufacture of dental restorations, where the dental restoration is manufactured by milling the restoration from a blank based on a digital restoration design which expresses a planned shape of the dental restoration. In order for such a dental restoration to be capable of being seated at the patient's existing teeth, the inner surface of the restoration must either be shaped according to the current shape of the existing teeth or according to the egg-shell design where a large volume is provided for the existing teeth at the inner surface of the restoration. The first approach requires that the shape of the existing teeth is known with high precision from e.g. a scanning of the teeth, while the second approach results in a dental restoration which has no surfaces to rest on and thus is difficult to arrange precisely in the mouth.

It remains a problem to provide a method, a user interface, and a system for creating digital designs for use in manufacturing a molding-shell for use in the forming a dental restoration.

When such a molding-shell which is arranged at the patient's teeth where the molding-shell and the tooth surface together define a volume for the dental restoration. The molding-shell approach does not have the problem of how to shape the inner surface of the dental restoration described above.

Disclosed is a method for generating a digital design for use in the manufacture of a molding-shell for a patient's teeth, where the molding-shell and the teeth together enclose a volume for forming a dental restoration, where the method comprises:

obtaining a digital 3D representation of the patient's teeth, said digital 3D representation comprising a tooth part relating to one or more teeth for which the dental restoration is formed;

obtaining a set of one or more digital teeth anatomies;

arranging the set of digital teeth anatomies and the digital 3D representation according to a preferred relative arrangement; and generating the digital design, where a first portion of the digital design is derived from the digital teeth anatomies and a second portion of the digital design is derived from the tooth part of the digital 3D representation.

The enclosed volume is defined by part of an inner surface of the molding-shell and part of the surface of the existing teeth.

In the context of the present application, the phases "inner surface of the shell" and "inner shell surface" refers to a tooth facing surface of a digital 3D representation of the molding-shell, such as of a digital molding-shell design, or of a manufactured molding-shell. I.e. the inner shell surface may be the surface of a manufactured molding-shell which faces the patient's teeth when the molding-shell is arranged at the teeth.

The formed dental restoration is configured for being seated at the patient's existing teeth with an inner surface contacting/facing the existing teeth.

When the formed dental restoration is arranged at the patient's teeth, the shape of the restored tooth or teeth is at least partly determined by the shape of the dental restoration and partly by the portion of the tooth which is not covered by the dental restoration.

In the preferred relative arrangement the digital teeth anatomies and the digital 3D representation are arranged relative to each other according to an anatomical correct arrangement.

This provides the advantage that various digital operations, such as collision line detection and Boolean addition or subtraction, can be performed. Further it provides that the digital teeth anatomies can be visualized together with the digital 3D representation of the corresponding teeth, i.e. the teeth which the manufactured dental restoration(s) will be seated on.

When the manufactured molding-shell is arranged at the teeth, a dental material can be injected into the enclosed volume. The volume is shaped according to a planned shape of the dental restoration such that when the injected dental material has hardened, the formed dental restoration has the planned shape. The planned shape of the dental restoration is such that when the dental restoration is seated on the existing teeth, the restored teeth take the form of the target shape.

The first portion of the inner surface of the manufactured molding-shell defines part of the boundary of the enclosed volume such that the outer surface of the formed restoration is shaped according to this first portion.

The second portion of the inner surface of the manufactured molding-shell can engage the patient's existing teeth to provide support for the molding-shell at the teeth. For a table-top restoration the second portion contacts the surface of the existing teeth which the table-top restoration is formed for.

The shape of the dental restoration is determined in part from the shape of the digital teeth anatomies and in part from the preferred relative arrangement of the digital teeth anatomies and the digital 3D representation of the teeth. The digital teeth anatomies express a planned shape of the part of the patient's teeth covered by the manufactured dental restoration.

In the context of the present application, the phrase "restored tooth/teeth" is used in relation to the tooth/teeth-restoration ensemble formed when the dental restoration is seated at the patient's existing tooth/teeth.

The inner surface of the formed restoration, i.e. the restoration surface which faces/contacts the existing teeth, is shaped according to the part of the boundary of the enclosed volume defined by the surface of the existing teeth. This provides an advantage of the molding-shell approach in that an exact knowledge of the shape of the existing teeth is not required in order to form a dental restoration which easily can be seated at the teeth.

In some embodiments, the digital design comprises a digital diagnostic wax-up. The digital diagnostic wax-up is for the manufacture of a physical diagnostic wax-up, i.e. a physical diagnostic wax-up can be manufactured from the digital diagnostic wax-up using Computer Aided Manufacture (CAM) equipment for direct digital manufacture, such as 3D printing or milling. The digital diagnostic wax-up expresses the target shape of the restored teeth. Accordingly, the physical diagnostic wax-up produced from the digital diagnostic wax-up will be shaped according to the target shape of the restored teeth.

When a physical diagnostic wax-up is produced, the molding-shell can be manufactured by shaping a molding-shell material using the physical diagnostic wax-up. The inner surface of the molding-shell will then be defined by the physical diagnostic wax-up and will thus have a shape according to the target shape of the restored teeth.

Given that the second portion of the digital diagnostic wax-up is shaped as a tooth part of the digital 3D representation, the inner surface of the formed molding-shell can rest on the corresponding part of the patient's teeth, where the line of contact between the molding-shell and the surface of the existing teeth define the cervical boundary of the enclosed volume for the dental restoration.

In some embodiments, the digital design comprises a digital molding-shell design. The digital molding-shell design is for direct digital manufacture of the molding-shell, such that a physical molding-shell can be manufactured directly from the digital molding-shell design without the use of an intermediate physical model, such as a diagnostic-wax up. This provides that the overall process for designing and manufacturing the molding-shell requires at least one step less than methods in which an intermediate model is required.

In some embodiments, the first and second portions define an inner shell surface of the digital molding-shell design.

The inner shell surface then expresses the target shape of part of the restored tooth or teeth. When a dental restoration is formed using the molding-shell and subsequently seated on the teeth, the restored tooth or teeth will then have the target shape.

In some embodiments, generating the digital design comprises creating an outer shell surface of the digital molding-shell design.

The outer shell surface may at least partly be created by copying the inner shell surface and offsetting the copied surface outwards.

In some embodiments, generating the digital molding-shell design comprises creating a connecting surface configured for connecting the inner and outer shell surfaces of the digital molding-shell design to generate a solid digital structure for the digital molding-shell design. The physical molding-shell can be manufactured from such a solid digital structure using CAM equipment.

The connecting surface may be created by a loofting process.

In order to provide a steadier placement of the molding-shell at the patient's existing teeth, the molding-shell may be provided with support structures that engage surfaces of the existing teeth to provide support for the molding-shell. The support structures may also aid the dentist when he arranges the molding-shell at the patient's teeth to ensure that the molding-shell is arranged correctly.

In some embodiments, the method comprises adding one or more digital support structures to the digital molding-shell design, where the digital support structures extend from the inner shell surface to the tooth part of the digital 3D representation.

In the molding-shell manufactured from the digital molding-shell design, the corresponding physical support structures provides the support for steady and/or correct arrangement of the molding-shell relative to the existing teeth.

The one or more support structures on the digital molding-shell design can be formed by a Boolean addition of a digital structure which extends from the surface of the digital diagnostic wax-up to the tooth part of the digital 3D representation.

In some embodiments, the method comprises defining one or more holes in the digital diagnostic wax-up, where the holes extend from the surface of the digital diagnostic wax-up to the tooth part of the digital 3D representation.

When a molding-shell material is arranged both in one of these holes and on the surface of the diagnostic wax-up the material forms a coherent structure, where the part of the structure shaped according to the hole defines the support structure. In the manufactured molding-shell the support structure allows for a steadier placement of the molding-shell at the patient's existing teeth.

The one or more holes in the digital diagnostic wax-up can be formed by a Boolean subtraction of a digital structure which extends from the surface of the digital diagnostic wax-up to the tooth part of the digital 3D representation.

In the formed dental restoration, the holes introduced by the support structures of the manufactured molding-shell can be filled with the dental material after the molding-shell has been removed.

In some embodiments, the manufactured molding-shell comprises a channel extending from the inner shell surface to the outer shell surface. The channel is preferably located such that it's opening on the inner shell surface terminates at the first portion and thus faces the enclosed volume. The channel will then allow passage of the dental material to and from the enclosed volume. The dentist may then choose to inject the dental material into the enclosed volume though the channel while the molding-shell is arranged at the teeth. Also if the dentist prefers to fill the molding-shell with the dental material for the dental restoration prior to arranging the filled shell at the teeth, the channel will allow excess dental material to escape such that the formed dental restoration can take the shape of the enclosed volume. Dental material located in the channel may stick to the dental restoration but this can easily be grinded/polished off to provide a smooth surface of the dental restoration.

In some embodiments, the method comprises defining a channel in the digital molding-shell design, where the channel extends from the inner shell surface to the outer shell surface. The channel preferably contacts the inner surface at the first portion of the digital molding-shell design.

In a molding-shell manufactured from such a digital molding-shell design the corresponding channel allows passage of the dental material to and from the enclosed volume.

In some embodiments, the method comprises defining a protrusion on the digital diagnostic wax-up.

The protrusion is arranged such that it points outwards from the digital diagnostic wax-up.

The protrusion may be formed on the digital diagnostic wax-up by a Boolean addition of a digital representation of the protrusion and the digital diagnostic wax-up. Alternatively, the protrusion may be defined on the part of the digital teeth anatomies from which the first portion of the digital diagnostic wax-up is formed. This provides that when the digital diagnostic wax-up is generated, the protrusion is already formed on the digital diagnostic wax-up.

When a diagnostic wax-up manufactured from such a digital diagnostic wax-up is used for the manufacture of the molding-shell, the corresponding physical protrusion on the diagnostic wax-up will define the channel in the material of the molding-shell.

The protrusion can be said to be a negative of the channel.

In some embodiments, generating the digital design comprises a Boolean addition of the digital 3D representation and the set of digital teeth anatomies.

The Boolean addition provides a digital structure with a surface expressing the target shape of the restored teeth, where the digital structure has a portion corresponding to the digital teeth anatomies and a portion corresponding to the surface of the tooth/teeth for which the dental restoration is formed. This digital structure may potentially also comprise portions relating to neighboring teeth and/or soft tissue such as the surrounding gingiva.

In some embodiments, the method comprises determining a line of contact for the digital 3D representation and the set of digital teeth anatomies, wherein the line of contact is derived from an intersection of the digital 3D representation and the digital teeth anatomies.

Deriving the line of contact with the digital teeth anatomies and the digital 3D representation arranged according to the preferred relative arrangement provides that the generating of the digital design can be made highly automatic.

When arranged at the teeth, the manufactured molding-shell contacts the teeth at the contact line which then defines a margin line of the formed dental restoration.

In some embodiments, the first portion of the digital design is derived from a portion of the set of digital teeth anatomies coronal to the line of contact.

This provides that the first portion is shaped according to the set of digital teeth anatomies. The choice of digital teeth anatomies thus influences the shape of digital design and thereby the outer surface of the formed dental restoration. The operator can hence determine the shape of this portion of the dental restoration by his selection of digital teeth anatomies.

In some embodiments, the second portion of the digital design is derived from a portion of the digital 3D representation cervical to the line of contact.

This provides that the second portion is shaped according to the tooth part of the digital 3D representation cervical to the line of contact and that the manufactured molding-shell can rest on this portion of the existing teeth. I.e. the molding-shell contacts the surface of the tooth for which the restoration is formed.

In some embodiments, the digital design comprises a third portion derived from a portion of the digital 3D representation corresponding to neighboring teeth and/or soft tissue.

This provides the advantage that the manufactured molding-shell can have a section adapted for resting on the neighboring teeth and/or soft tissue, i.e. on the teeth surrounding the tooth/teeth for which the dental restoration is formed.

In some embodiments, the method comprises creating a digital restoration design for the dental restoration, where the digital restoration design expresses the planned shape of the dental restoration.

This provides the advantage that the digital restoration design can be visualized, optionally together with the patient's existing teeth, such that the operator can evaluate whether the planned shape of the dental restoration is adequate e.g. with respect to minimum thickness criteria and aesthetic properties.

In some embodiments, the digital restoration design is created based on the digital teeth anatomies and the digital 3D representation of the patient's teeth when these are arranged according to the preferred relative arrangement. E.g. the digital restoration design is created can be created by a Boolean subtraction of the digital 3D representation of the patient's teeth from the digital teeth anatomies.

The digital restoration design may comprise a restoration margin line. In some embodiments, the restoration margin line is derived from the line of contact between the digital teeth anatomies and the digital 3D representation of the patient's teeth. The restoration margin line can thus be determined automatically without the need for the operator to use time to manually define it.

The digital restoration design may be designed to improve the aesthetics and function of the patient's set of teeth. With respect to the function it can be advantageous to analyze the bite of the patient's restored teeth using a virtual articulator which mimics the relative movements of the patient's jaws during a bite.

In some embodiments, an inner restoration surface of the dental restoration design is shaped according to portions of the existing teeth coronal to the line of contact while the outer surface of the dental restoration is shaped according to the digital teeth anatomies.

In some embodiments, at least part of the first portion of the digital design is created from the digital restoration design.

Given that the digital restoration design is crated from the digital teeth anatomies, this provides that first portion of the digital design is derived from the digital teeth anatomies.

In some embodiments the molding-shell is for forming a table-top restoration, an onlay, an inlay, a crown, a bridge, or a veneer, such as a minimum-preparation veneer.

The dental restoration may be a table-top restoration configured for raising the patient's bite. Table-top restorations are frequently used when the occlusal table of the patient's teeth is severely worn. The table-top restoration is shaped to be seated on top of the teeth where it raises the patient's bite. There is hence no need for preparing the tooth by grinding away substantial amounts of tooth material and the second portion of the digital design can be defined from a tooth part of a digital 3D representation of the patent's teeth. The same is true for the so-called minimum-preparation veneers which comprise a relatively thin layer of restoration material shaped to cover part of the labial and buccal surfaces of the teeth in order to improve the aesthetics of the teeth.

The table-top teeth can be a temporary restoration worn by the patient for a period of time in which period the patient's muscles are trained for the raised bite. This may be applicable to patients having problems with the temporomandibular joint (TMJ) and where the occlusal surface of e.g. the teeth of the mandibular jaw must be raised to treat the problem. After a period of time, e.g. some months, the dentist evaluates whether the raised bite is appropriate and solves the TMJ problems.

When the patient is not pleased with the appearance of his teeth he may wish to have a veneer designed and manufactured for his teeth. The patient may still have all his teeth in their original and unprepared shape but desires a more appealing smile. A veneer is often designed and manufactured for the anterior teeth which are the most visible of the patient's teeth.

In some embodiments the digital design is for the manufacture of a molding-shell for a minimum-preparation veneer.

The dental restoration may be a crown restoration for a damaged tooth, where the crown is configured for being seated at a slightly prepared tooth.

Deriving the intersection of the digital 3D representation and the digital teeth anatomies and detecting the line of contact from the intersection are preferably performed by computer implemented algorithms executed on e.g. a microprocessor. This provides the advantage that the operator does not need to manually define the line of contact and the design process can be accelerated. This advantage is obtained when the manufactured dental restoration is to be arranged on a patient's existing tooth/teeth. In contrast, when the dental restoration is e.g. a crown for a fully prepared tooth a restoration margin line must be defined for the crown, where the restoration margin line precisely must match the preparation line of the prepared tooth in order to avoid e.g. a grove at the transition between the dental restoration and the prepared tooth causing discomfort and the risk of bacteria being caught.

In some cases the operator may choose to make slight modifications to the line of contact but this is often not required. An example of such a modification is the smoothing of the line of contact to provide a smooth transition between the first and second portions of the digital design, such that e.g. the diagnostic wax-up or the molding-shell is easier to manufacture from the digital design. The digital design may be modified in response to such a modification, e.g. by making slight changes in the parts of the digital teeth anatomies and the tooth part of the digital 3D representation used in forming the first and second portions of the digital design. In some cases it may be necessary to apply a loofting process to connect the modified first and second portions of the digital design to form complete and watertight digital design.

The determined line of contact divides the digital teeth anatomies into a coronal part and a cervical/apical part, where the coronal part forms the first portion of the generated digital design. In some embodiments, the method comprises digitally removing portions of the digital teeth anatomies cervical/apical to the line of contact and using the thus truncated digital teeth anatomies in generating the digital design.

In the context of the present invention, the phrase "Item 1 being coronal to Item 2" refers to the situation where Item 1 is closer to the occlusal surface/incisal edge of a tooth than Item 2. In the context of the present invention, the phrase "Item 1 being cervical/apical to Item 2" refers to the situation where Item 1 is closer to the root part of the tooth, i.e. where item 2 is closer to the occlusal surface/incisal edge of a tooth than Item 1.

The line of contact separates the coronal and cervical portions of the tooth part of the digital 3D representation. In some embodiments, the method comprises digitally removing portions of the digital 3D representation coronal to the line of contact and using the thus truncated digital 3D representation as the second portion in creating the digital design.

The inner and outer surfaces of a digital restoration design may be based on coronal portions of the digital 3D representation and of the digital teeth anatomies, respectively, where the coronal portions may be bounded by the determined line of contact.

In some embodiments, creating the first and second portions of the digital design comprises copying the corresponding sections of the digital teeth anatomies and of the tooth part of the digital 3D representation. The copied sections may further be modified according to the operators experience and preferences.

In some embodiments, the sections of the digital teeth anatomies and of the tooth part of the digital 3D representation which are used in generating the digital restoration design are coronal to the detected line of contact such that determined line of contact defines a restoration margin line for the formed dental restoration.

In some embodiments, creating the digital restoration design comprises a Boolean subtraction of the digital 3D representation from the digital teeth anatomies.

The intersection of the digital 3D representation and the digital teeth anatomies is automatically defined in the Boolean subtraction. Creating the digital restoration design by such a Boolean subtraction has the advantage that the restoration margin line is automatically derived. The shape and position of the restoration margin line depends on the digital teeth anatomies, the digital 3D representation and the preferred relative arrangement.

A Boolean subtraction of a first solid digital structure from a second solid digital structure provides that a third solid digital structure is generated where the third solid digital structure is shaped according to the second solid digital structure where the parts shared with the first solid digital structure are removed.

The Boolean subtraction of the solid digital structures may correspond to determining their relative complement, such that the digital restoration design resulting from the Boolean subtraction is the part of the digital teeth anatomies which is not shared with the digital 3D representation. Thereby the created inner surface of the digital restoration design is shaped according to the shape of the corresponding part of the digital 3D representation while the outer surface of the digital restoration design is shaped according to the shape of the digital teeth anatomies. The inner surface of the digital restoration design is thus at least in part created by determining the relative complement of the digital 3D representation in the digital teeth anatomies.

The distance between a point on the first portion of the digital design and the nearest point on the digital 3D representation provides a measure of the planned thickness of the formed dental restoration at this point. Alternatively, the planned thickness can be measured from the digital teeth anatomies to the digital 3D representation. I.e. in some embodiments, the method comprises determining a planned thickness of the dental restoration as the distance from the digital 3D representation of the patient's teeth to the digital design or to the digital teeth anatomies In some embodiments, the method comprises examining the planned thickness with respect to one or more minimum thickness criteria to identify any problematic regions.

In some embodiments, the method comprises examining the digital restoration design with respect to one or more minimum thickness criteria to identify any problematic regions of the dental restoration.

A problematic region may be a region of the digital design where the planned thickness is below that specified by the minimum thickness criteria. In the formed dental restoration the corresponding region will be so thin that the dental restoration may be fragile.

Examining the planned thickness with respect to one or more minimum thickness criteria provides the advantage that the operator can be warned that the current shape of the digital design will provide a fragile dental restoration.

In some embodiments the method comprises adjusting the first portion of the digital design in the problematic regions to provide that the minimum thickness criteria are met in these regions.

This has the advantage that the formed dental restoration will be robust and have no fragile regions.

In some embodiments the adjusting comprises:
  modifying the first portion such that the planned thickness is increased in the problematic region and the minimum thickness criteria are met; and/or
  extending the second portion of the digital design to a point where the minimum thickness criteria are met and truncating the first portion accordingly.

Both increasing the planned thickness and extending the second portion in the problematic region provide the advantage that the formed dental restoration is free of problematic regions causing fragile regions where it otherwise may break easily.

In some embodiments the method comprises defining an offset surface by offsetting at least part of the digital 3D representation a distance according to the minimum thickness criteria. The offset is directed outwards relative to the surfaces of the digital 3D representation. For instance if a minimum thickness criterion dictates a minimum thickness of 0.5 mm the offset surface can be formed by offsetting the surface of the digital 3D representation outwards by 0.5 mm. The value of this number may depend on the dental material used for forming the dental restoration.

The offset surface can be used when examining the first portion of the digital design and/or the digital restoration design to identify problematic regions where the minimum thickness criteria are not fulfilled. This can be realized by identifying the portions of the first portion or of the digital teeth anatomies which are located between the digital 3D representation and the offset surface. Such portions will not fulfill the minimum thickness criteria.

If problematic regions are found, the offset surface can be used for the adjustment of the first portion of the digital design such as by modifying it to follow the offset surface at least in part of the problematic regions. The problematic regions of the first portion can e.g. be snapped onto the offset surface, i.e. shaped to follow the offset surface, whereby it is provided that the planned thickness is increased to a level where the minimum thickness criteria also are fulfilled in those regions.

The offset surface can also be used to determine the point where the minimum thickness criteria are met, such that the second portion of the digital design can be extended to this to provide that the minimum thickness criteria are fulfilled for all regions. This point may be where the offset surface intersects the digital teeth anatomies.

In some embodiments the digital restoration design is for manufacture of the molding-shell by milling and the method comprises adjusting the digital design to provide for drill compensation.

In the context of the present invention, the phrase "to provide for drill compensation" refers to the case where the digital design is adjusted such that the shape of the drill which is to be used is taken into consideration.

When the tip of the drill has a curvature it cannot form e.g. a 90 degrees bend. When attempting to form sharp bends some material will be remaining. For a molding-shell with an inner surface shaped according to a planned shape of the dental restoration this remaining material may cause that a section of the formed dental restoration is missing.

In some embodiments the drill compensation is provided by introducing one or more indentations in the digital design e.g. where a support structure raises from the first portion of a digital molding-shell design. The indentations will cause that the inner surface of the manufactured molding-shell has indentations and accordingly that protrusions are defined on the surface of the formed dental restoration. The excess restoration material can however be grinded and/or polished away such that the final dental restoration is shaped according to the planned shape.

In some embodiments, the cross-sectional size of the indentation is chosen to be larger than or equal to the diameter of the drill which is to be used in the manufacture of the dental restoration. For an indentation with a circular cross-section, the cross sectional size is the diameter of the indentation.

In some embodiments the method comprises adjusting the curvature of the digital design at the line of contact to match the curvature of the digital 3D representation of the patient's teeth.

A large mismatch in curvature can make the interface between the dental restoration and the existing teeth clearly visible. The curvature adjustment may provide a smoother and less visible transition from teeth to dental restoration and thus improve the appearance of the restored tooth/teeth.

In some embodiments obtaining the digital teeth anatomies comprises selecting a set of library teeth.

This has the advantage that the digital teeth anatomies can be obtained faster than when the operator himself designs the surfaces of the digital teeth anatomies.

Disclosed is a method for generating a digital design for use in the manufacture of a molding-shell for a patient's teeth, where the molding-shell and the teeth together enclose a volume for forming a dental restoration, where the method comprises:

loading a digital 3D representation of the patient's teeth into an electronic data processing device, said digital 3D representation comprising a tooth part relating to one or more teeth for which the dental restoration is formed;

loading a set of one or more digital teeth anatomies into the electronic data processing device;

arranging the set of digital teeth anatomies and the digital 3D representation according to a preferred relative arrangement; and using said electronic data processing device to execute computer implemented algorithms configured for generating the digital design where a first portion of the digital design is derived from the digital teeth anatomies and a second portion of the digital design is derived from the tooth part of the digital 3D representation.

The electronic data processing device can be a computer processor such as a microprocessor.

Disclosed is a user interface for generating a digital design for use in the manufacture of a molding-shell for a patient's teeth, where the molding-shell and the teeth together enclose a volume for forming a dental restoration, where the user interface is configured for:

obtaining a digital 3D representation of the patient's teeth, said digital 3D representation comprising a tooth part relating to one or more teeth for which the dental restoration is formed;

obtaining a set of one or more digital teeth anatomies;

arranging the set of digital teeth anatomies and the digital 3D representation according to a preferred relative arrangement; and generating the digital design where a first portion of the digital design is derived from the digital teeth anatomies and a second portion of the digital design is derived from the tooth part of the digital 3D representation.

In some embodiments, the user interface comprises a virtual push button configured for generated the digital design when activated.

The digital design can be generated using a method according to any of the embodiments. For example the digital design can be a digital diagnostic wax-up generated by a Boolean addition of the digital teeth anatomies and the tooth part of the digital 3D representation.

In some embodiments, the user interface is configured for being visualized to an operator using a visual display unit and for allowing an operator to enter data into and make choices presented in the user interface by means of a computer keyboard or a computer mouse.

In some embodiments, the user interface comprises a data entering section for entering data relating to e.g. whether the generated digital design shall be a digital molding-shell design or a digital diagnostic wax-up, and whether the digital design is to be created from a determined line of contact or by a Boolean addition.

In some embodiments, the user interface is configured for visualizing the created digital design.

Disclosed is a method for manufacturing a molding-shell for a patient's teeth, where the molding-shell and the teeth together enclose a volume for forming a dental restoration, where the method comprises:

generating a digital design using a method according to any of the embodiments, and manufacturing a physical copy of the digital design using direct digital manufacture equipment.

In some embodiments, the digital design comprises a digital diagnostic wax-up such that the manufactured physical copy comprises a physical diagnostic wax-up, and the method comprises arranging a molding-shell material at the manufactured physical diagnostic wax-up such that the molding-shell is manufactured with an inner surface shape defined by the physical diagnostic wax-up.

In some embodiments, the digital design comprises a digital molding-shell design such that the physical copy manufactured from the digital design comprises the molding-shell.

Disclosed is a method for manufacturing a molding-shell for a patient's teeth, where the molding-shell and the teeth together enclose a volume for forming a dental restoration, where the method comprises:

obtaining a digital 3D representation of the patient's teeth, said digital 3D representation comprising a tooth part relating to one or more teeth for which the dental restoration is formed;

obtaining a set of one or more digital teeth anatomies;

arranging the set of digital teeth anatomies and the digital 3D representation according to a preferred relative arrangement; and generating the digital design where a first portion of the digital design is derived from the digital teeth anatomies and a second portion of the digital design is derived from the tooth part of the digital 3D representation.

In some embodiments, the digital design comprises a digital diagnostic wax-up and the method comprises manufacturing a physical diagnostic wax-up from the digital diagnostic wax-up and arranging a molding-shell material at the manufactured physical diagnostic wax-up, such that the molding-shell is manufactured with an inner surface shape defined by the physical diagnostic wax-up.

In some embodiments, the digital design comprises a digital molding-shell design where the first and second portions define an inner shell surface of the digital molding-shell design, and the method comprises:

forming a solid digital structure for the digital molding-shell design based at least partly on the inner shell surface, and manufacturing the molding-shell from the solid digital structure.

Disclosed is a method for generating a digital design for use in the manufacture of a molding-shell for a patient's teeth, where the molding-shell and the teeth together enclose a volume for forming a dental restoration, where the method comprises:

obtaining a digital 3D representation of the patient's teeth, said digital 3D representation comprising a tooth part relating to one or more teeth for which the dental restoration is formed;

designing a digital restoration design at the digital 3D representation where the digital restoration design express a planned shape of the dental restoration; and generating the digital design, where a first portion of the digital design is derived from the digital restoration design and a second portion of the digital design is derived from the tooth part of the digital 3D representation.

In some embodiments, obtaining the digital 3D representation of the patient's teeth comprises loading the digital 3D representation into an electronic data processing device and generating the digital design comprises executing computer implemented algorithms on the electronic data processing device, where the algorithms are configured for generating the digital design at least partly from the digital 3D representation of the patient's teeth and the digital restoration design.

Disclosed is a user interface for generating a digital design for use in the manufacture of a molding-shell for a patient's teeth, where the molding-shell and the teeth together enclose a volume for forming a dental restoration, where the user interface is configured for:
- obtaining a digital 3D representation of the patient's teeth, said digital 3D representation comprising a tooth part relating to one or more teeth for which the dental restoration is formed;
- designing a digital restoration design at the digital 3D representation where the digital restoration design express a planned shape of the dental restoration; and
- generating the digital design, where a first portion of the digital design is derived from the digital restoration design and a second portion of the digital design is derived from the tooth part of the digital 3D representation.

Disclosed is a system for designing a digital design for manufacturing a molding-shell for a patient's teeth, where the molding-shell and the teeth together enclose a volume for forming a dental restoration, wherein the system comprises:
- a computer device comprising a non-transitory computer readable medium and an electronic data processing device, where said computer device is capable of obtaining a set of one or more digital teeth anatomies and a digital 3D representation of the patient's teeth, where said digital 3D representation comprises a tooth part relating to one or more teeth for which the dental restoration is formed;
- a visual display unit for displaying the digital teeth anatomies and the digital 3D representation of the patient's teeth; and
- digital tools allowing an operator to arrange the set of digital teeth anatomies and the digital 3D representation according to a preferred relative arrangement;

where the computer readable medium comprises computer code which when executed on the electronic data processing device generates the digital design, where a first portion of the digital design is derived from the digital teeth anatomies and a second portion of the digital design is derived from the tooth part of the digital 3D representation.

Disclosed is a system for designing a digital design for manufacturing a molding-shell for a patient's teeth, where the molding-shell and the teeth together enclose a volume for forming a dental restoration, wherein the system comprises:
- a computer device comprising a non-transitory computer readable medium and an electronic data processing device, where said computer device is capable of obtaining a digital 3D representation of the patient's teeth, where said digital 3D representation comprises a tooth part relating to one or more teeth for which the dental restoration is formed;
- a visual display unit for displaying the digital 3D representation of the patient's teeth and a digital restoration design expressing a planned shape of the dental restoration; and
- digital tools allowing an operator to design the digital restoration design at the digital 3D representation;

where the computer readable medium comprises computer code which when executed on the electronic data processing device generates the digital design, where a first portion of the digital design is derived from the digital restoration design and a second portion of the digital design is derived from the tooth part of the digital 3D representation.

As described above the digital design may be for direct digital manufacture of the structure described by the digital design using CAM equipment.

When the digital design is a digital molding-shell design the molding shell is preferably manufactured directly from the digital design by the system. The digital design may also be for manufacture of a diagnostic wax-up expressing a target shape of the restored teeth such that the molding-shell is formed by applying molding-shell material to the surface of the manufactured diagnostic wax-up.

The digital tools of the system may comprise a pointing tool, such as a computer mouse, and a keyboard.

When a direct digital manufacture unit, such as CAM equipment, is included in the system it can be used as a system for manufacturing the molding-shell for a patient's teeth.

BRIEF DESCRIPTION OF THE DRAWINGS

The above and/or additional objects, features and advantages of the present disclosure, will be further elucidated by the following illustrative and non-limiting detailed description of various embodiments, with reference to the appended drawings, wherein:

FIGS. 1A-1C show exemplary workflows.

DETAILED DESCRIPTION

In the following description, reference is made to the accompanying figures, which show by way of illustration how the disclosed methods and systems may be practiced.

FIG. 1 shows examples of workflows for embodiments.

Figure 1A:
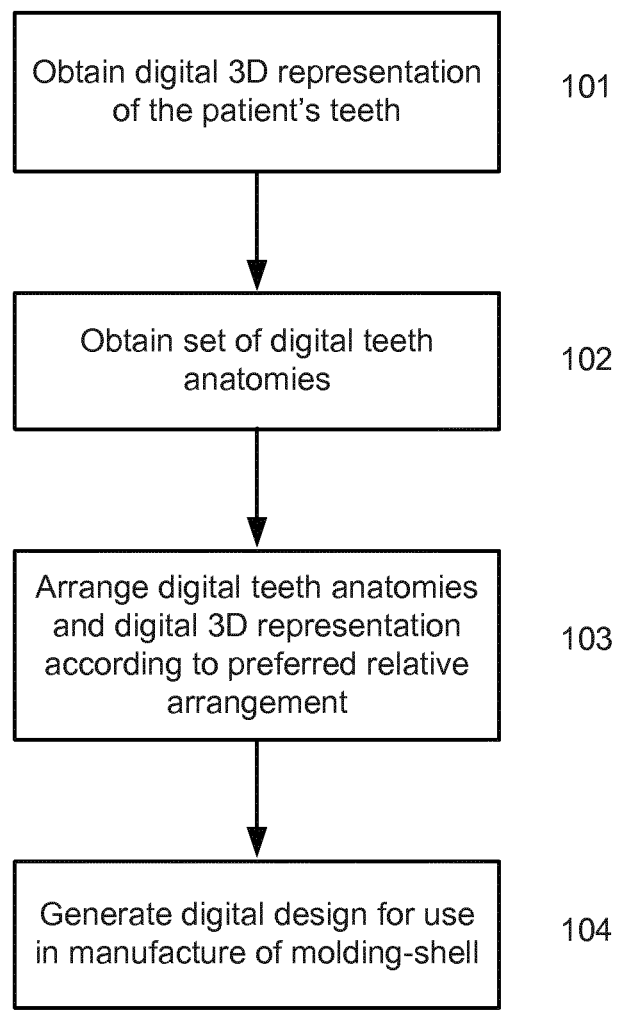

FIG. 1A illustrates a workflow 100 according to one embodiment in which a digital design is generated. The digital design is for use in the manufacture of a molding-shell for a patient's teeth. When the manufactured molding-shell is arranged at the teeth the molding-shell and the teeth together enclose a volume for forming a dental restoration.

In step 101 a digital 3D representation of the patient's teeth is obtained, where the digital 3D representation comprises a tooth part relating to one or more teeth for which the dental restoration is formed.

The digital 3D representation can e.g. be obtained using an intraoral 3D scanner such as the TRIOS intraoral scanner provided by 3shape A/S where the teeth are scanned directly in the patient's mouth. The digital 3D representation can also be obtained by scanning an impression of the teeth or by scanning a physical model of the teeth obtained using such an impression.

The digital 3D representation can be of the patient's entire set of teeth or a part of the set of teeth, such as a part of the teeth in the upper and/or lower jaw. The digital 3D representation provides information relating to at least the geometry of the teeth.

In step 102 a set of one or more digital teeth anatomies is obtained. The digital teeth anatomies can be a set of library teeth selected from a library of digital template teeth.

In step 103, the set of digital teeth anatomies and the digital 3D representation are arranged in relation to each other according to a preferred relative arrangement.

The antagonist teeth can be taken into consideration when selecting or designing the digital teeth anatomies as well as when arranging the digital teeth anatomies and the digital 3D representation in relation to each other. This can include analyzing the occlusion of the digital teeth anatomies with a digital 3D representation of the antagonist teeth using e.g. a virtual articulator to mimic the relative movement of the patient's jaws in a bite.

One way of arranging the digital teeth anatomies and the digital 3D representation in relation to each other is to determine a transformation matrix for mapping the two into the same coordinate system. This may e.g. be a transformation matrix for mapping the digital teeth anatomies into the coordinate system of the digital 3D representation, or vice versa. It may also be transformation matrices for mapping the two into another coordinate system, such as the coordinate system of a virtual articulator used for digitally analyzing the relative movement of the patient's mandibular and maxillary teeth during jaw motion.

When the digital teeth anatomies and the digital 3D representation are expressed in the same coordinate system they can also be visualized to an operator using e.g. a computer screen.

In the preferred relative arrangement, the digital teeth anatomies and the tooth part of the digital 3D representation together express a target shape of the restored teeth, i.e. the effective shape of the patient's teeth when the formed dental restoration is seated thereon.

In step 104 the digital design is generated, where the generated digital design comprises a first portion derived from the digital teeth anatomies and a second portion derived from the tooth part of the digital 3D representation.

Figure 1B:
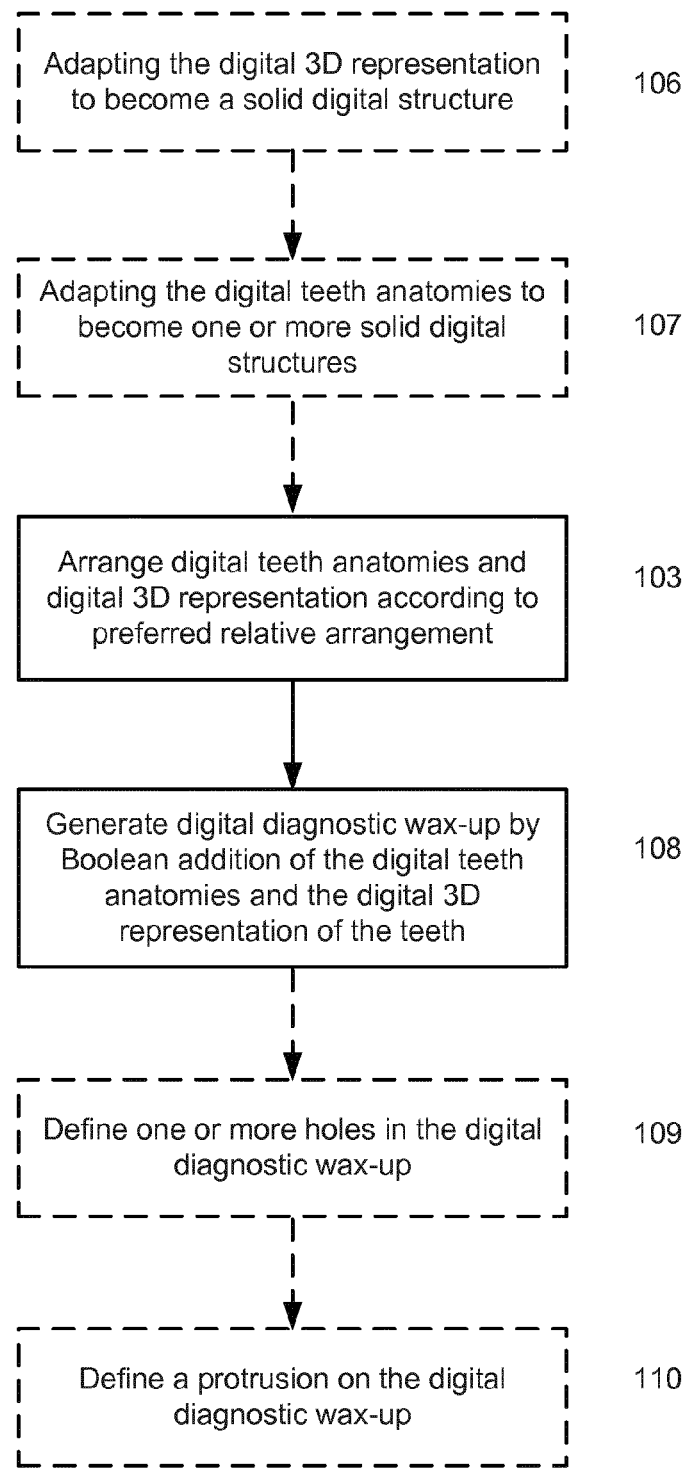

FIG. 1B illustrates steps of a workflow 105 for an embodiment of the method, where the digital design is a digital diagnostic wax-up for the manufacture of a physical diagnostic wax-up.

In step 106 the digital 3D representation is adapted to become a solid digital structure. The digital 3D representation can e.g. be a polygonal mesh provided by the 3D scanner and provides information relating to the geometry/shape of the patient's teeth and possibly the surrounding gingiva. From this polygonal mesh a digital solid structure for the digital 3D representation can be formed. The formed solid digital structure can be used in Constructive Solid Geometry (CSG) for creating the digital design using e.g. a computer implemented Boolean algorithms.

In some cases, the digital 3D representation obtained from the 3D scanner is already a solid digital structure such that step 106 not is required.

In step 107 the digital teeth anatomies are adapted to become one or more solid digital structures. Often the digital teeth anatomies selected from a teeth library are already in the form of one or more solid digital structures such that step 107 not is required.

In step 103, the digital teeth anatomies and the digital 3D representation are arranged according to a preferred relative arrangement as described above in relation to FIG. 1A.

In step 108 the digital diagnostic wax-up is generated by a Boolean addition of the digital 3D representation and the digital teeth anatomies.

A physical copy of the digital design, i.e. a physical diagnostic wax-up, can be manufactured using CAM equipment. Since the digital diagnostic wax-up formed by the Boolean addition is shaped according to the target shape of the restored teeth the corresponding part of a physical diagnostic wax-up manufactured from the generated digital design diagnostic wax-up will have a shape according to the target shape. If a molding material is arranged in contact with this physical diagnostic wax-up to form a molding-shell, the molding-shell will have a surface which is shaped according to the target shape of the restored teeth. When arranging this molding-shell at the teeth a volume for the dental restoration is enclosed.

Some additional optional steps may improve the digital diagnostic wax-up such that the manufactured diagnostic wax-up has some additional features.

In step 109 one or more holes are defined in the digital diagnostic wax-up, where the holes extend from the surface of the digital diagnostic wax-up to the tooth part of the digital 3D representation.

When the molding-shell material is arranged at the manufactured diagnostic wax-up, the molding-shell material which enters these holes will form support structures on the manufactured molding-shell. These support structures will extend from the inner surface of the shell to the patient's existing teeth and thereby provide support for the molding-shell.

In step 110 a protrusion is defined on the digital diagnostic wax-up. When the molding-shell material is arranged at the manufactured diagnostic wax-up, the protrusion will form a channel in the molding-shell material such that when the manufactured molding-shell is arranged at the teeth, the channel provides an inlet for the dental material used to form the dental restoration. Alternatively, the channel can provide an outlet for excess dental material when arranging a filled molding-shell at the teeth.

FIG. 1C illustrates steps of a workflow 111 wherein the digital design is a digital molding-shell design for direct digital manufacture of the molding-shell.

Prior to the steps described in the following, the set of digital teeth anatomies and the digital 3D representation have been obtained and arranged according to the preferred relative arrangement. This can be done with the steps described above in connection with FIG. 1A.

In step 112 a line of contact between the digital 3D representation and the set of digital teeth anatomies is detected from an intersection of the digital 3D representation and the digital teeth anatomies.

In step 113 the first portion of the digital design is derived from a section of the set of digital teeth anatomies coronal to the line of contact.

In step 114 the second portion of the digital design is derived from a section of the digital 3D representation cervical to the line of contact, where at least part of this section corresponds to the surface of the existing teeth for which the dental restoration is formed.

In step 115 the inner surface of the digital molding-shell design is created from the first and second portions. I.e.

together, the derived first and second portions define the inner shell surface of the digital molding-shell design.

In step 116 an outer shell surface of the digital molding-shell design is created. The outer shell surface can be formed by copying and offsetting the inner surface created in step 115.

With the outer and inner surface of the digital molding-shell design formed, a solid digital structure for the digital molding-shell design can be formed by closing any gap between the inner and outer shell surfaces, e.g. by forming a connecting surface using a computer implemented loofting algorithm.

As also described in relation to the digital diagnostic wax-up above some additional optional steps may improve the digital molding-shell design such that the manufactured molding-shell has some additional advantageous features.

In step 117 one or more digital support structures are added to the digital molding-shell design where the digital support structures extend from the inner shell surface to the tooth part of the digital 3D representation.

In the molding-shell manufactured from the digital molding-shell design the corresponding physical support structures will extend from the inner surface of the molding-shell to the patient's existing teeth and thereby provide support for the molding-shell.

In step 118 a channel is defined in the digital molding-shell design, where the channel extends from the inner shell surface to the outer shell surface. When the manufactured molding-shell is arranged at the teeth, the corresponding physical channel provides an inlet for the dental material used to form the dental restoration. Alternatively, the channel can provide an outlet for excess dental material when arranging a filled molding-shell at the teeth.

The first and second portions of the digital molding-shell design can also be generated by the Boolean addition of the digital 3D representation and the set of digital teeth anatomies described above in relation to FIG. 1B. Part of the surface of the digital diagnostic wax-up generated by the Boolean addition of the digital 3D representation and the digital teeth anatomies (step 108 above) is then inverted to become the inner surface of the molding shell and the outer surface can be generated by the offset mentioned above.

A physical copy of the digital molding shell design, i.e. the molding-shell, can be manufactured from the digital design using CAM equipment.

Likewise, first and second portions of the digital diagnostic wax-up in FIG. 1B can also be created by determining a line of contact for the digital 3D representation and the set of digital teeth anatomies, and deriving the first portion from a section of the set of digital teeth anatomies coronal to the line of contact and the second portion from a section of the digital 3D representation cervical to the line of contact.

Figure 2:
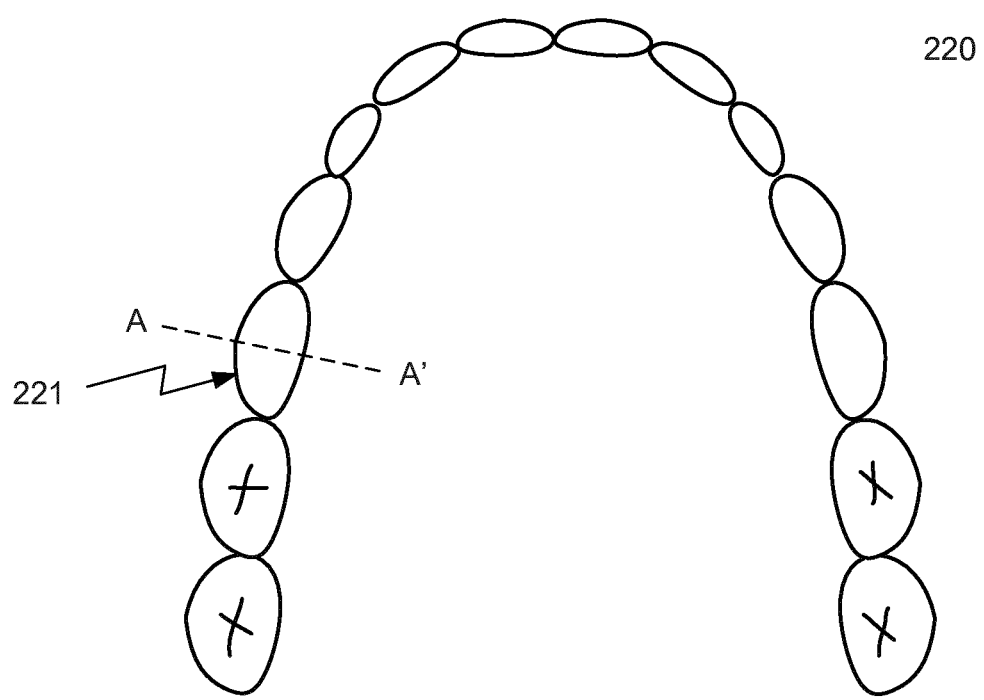
FIG. 2 shows a schematic of the existing teeth in one of the patient's jaws.

FIG. 2 shows a schematic of the teeth in the patient's mandibular jaw.

The schematic shows the patient's existing teeth 220 with anterior teeth in the top of the figure and molars at the bottom. The line A-A' crossing one tooth 221 marks a cross sectional plane which extends along the normal to the occlusal plane of the set of teeth, i.e. the cross sectional plane is perpendicular to the patient's occlusal plane.

FIGS. 3 to 7 show schematics of digital 3D representations of the patient's existing teeth, digital designs and different surfaces depicted as cross sections in a plane such as the one defined in FIG. 2.

Figure 3A:
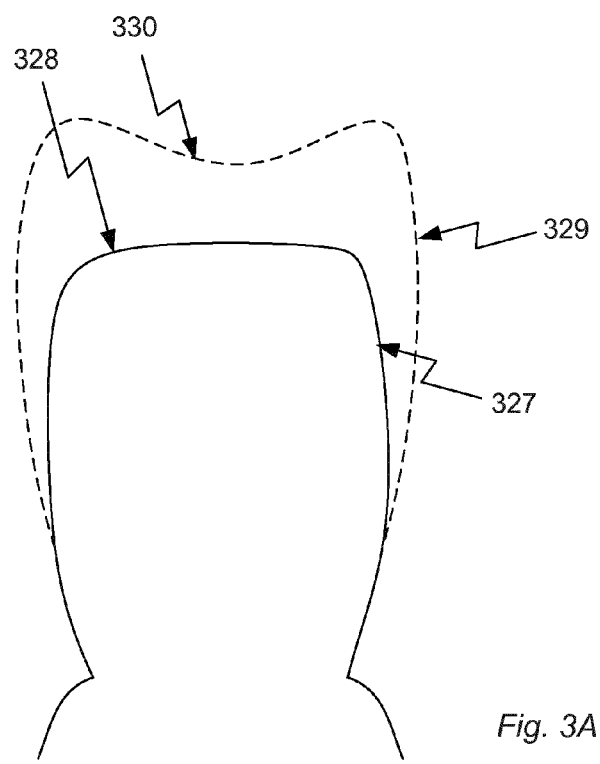
FIGS. 3A-3B show a schematic of a cross-section of the patient's teeth and of a dental restoration.

FIG. 3A shows a schematic of a cross-section of the patient's teeth at a plane such as the A-A' plane seen in FIG. 2. The full line shows the shape of the existing teeth in their current state 327 while the dotted line shows the original shape 329 of the teeth. The teeth are severely worn so that the current occlusal surface 328 is much lower than the original occlusal surface 330. This causes discomfort to the patient and an unnatural strain on the muscles active during e.g. mastication.

Figure 3B:
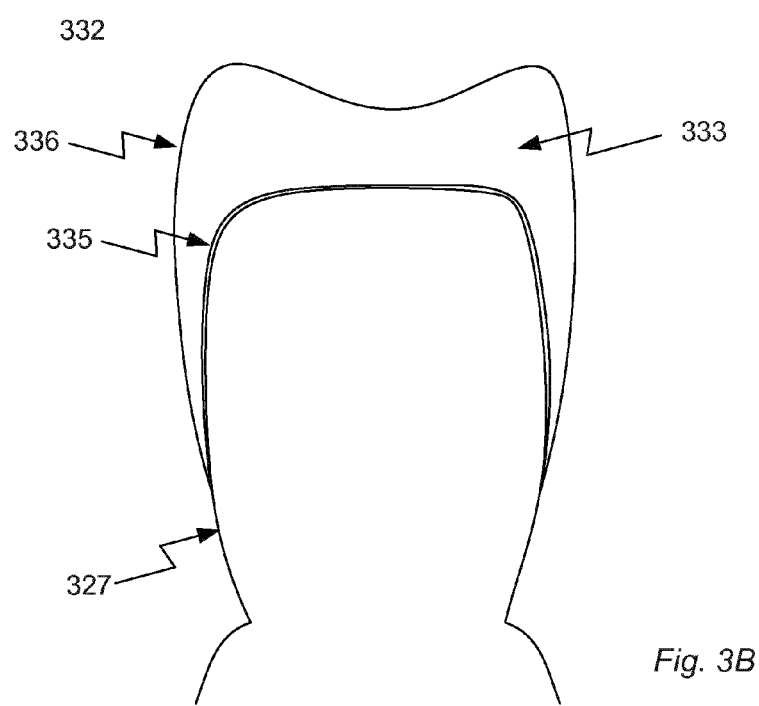

FIG. 3B shows a schematic of a manufactured table-top restoration 333 arranged on the worn tooth illustrated in FIG. 3A.

The restoration 333 is a table-top restoration designed to raise the occlusal table of the worn tooth 327. It has an inner surface 335 shaped to engage the surface of the worn tooth 327 and an outer surface 336 shaped to defined the raised occlusal table and engage the antagonist teeth when the patient's bites. The table-top restoration 333 increases the length of the patient's teeth and when the patient uses the restoration the muscles get used to the raised bite defined by the table-top restoration. The visible part of the worn tooth 327 and the outer surface 336 of the dental restoration 333 defines the shape of the restored tooth 332.

FIG. 4 shows a schematic of a case where the digital design is a digital diagnostic wax-up formed by Boolean addition.

Figure 4A:
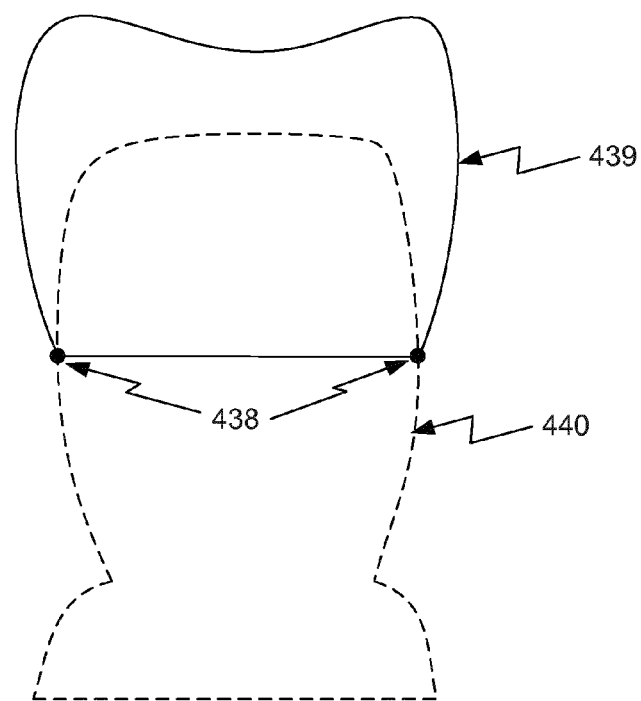
FIGS. 4A-4D show a schematic of a case where the digital design is a digital diagnostic wax-up formed by Boolean addition.

In FIG. 4A the obtained digital teeth anatomies 439 (solid line) and the digital 3D representation 440 (dotted line) are in the form of solid digital structures. The digital teeth anatomies can be obtained from a library of template teeth based on the dentist's preference, while the digital 3D representation can be obtained by different means such as by intra-oral scanning of the patient's teeth using e.g. the TRIOS intra-oral scanner by 3shape A/S or by scanning an impression of the teeth or a physical model made from such an impression.

The two solid digital structures are expressed in a common coordinate system according to their preferred relative arrangement. The common coordinate system may e.g. be that in which the digital 3D representation already is expressed. The digital 3D representation 440 has a tooth part relating to one or more teeth for which the dental restoration is formed.

The intersection of the two solid digital structures defines a line of contact 438. The margin line of a dental restoration formed using the manufactured molding-shell is shaped according to the line of contact.

Figure 4B:
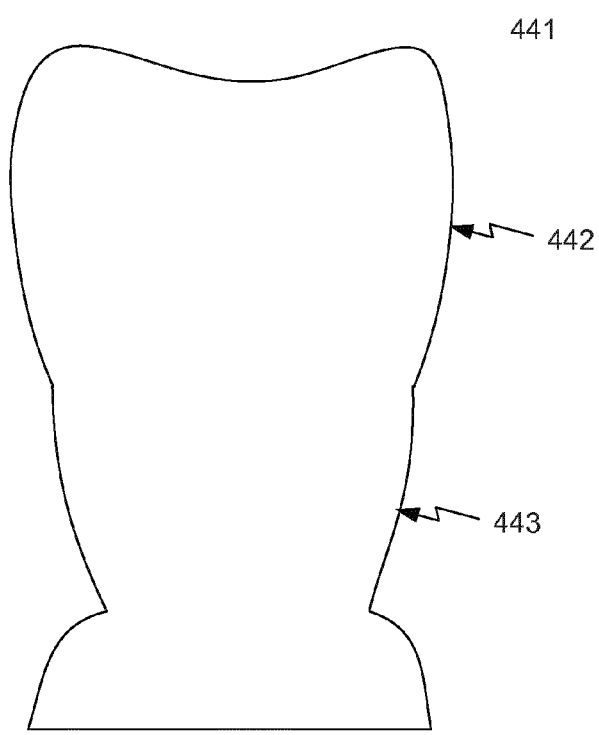

In FIG. 4B the digital design 441 is a digital diagnostic wax-up generated by a Boolean addition of the digital 3D representation and the set of digital teeth anatomies. The digital diagnostic wax-up has a first portion 442 shaped according to a section of the digital teeth anatomies and a second portion 443 shaped according to a section of the tooth part of the digital 3D representation. The digital diagnostic wax-up express the target shape of the restored teeth, i.e. the effective shape of the patient's teeth when the formed dental restoration is arranged at the existing teeth.

Figure 4C:
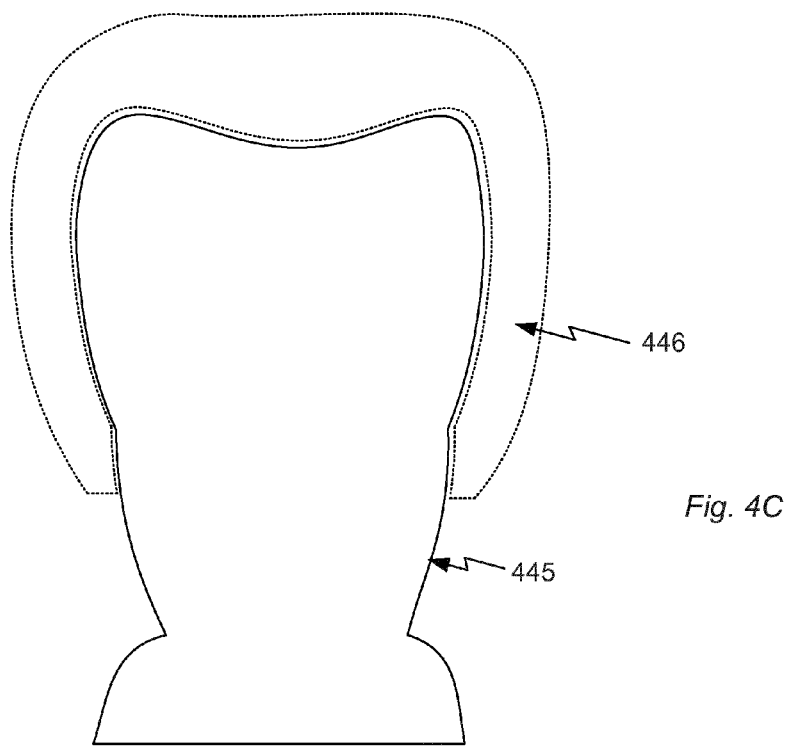

A physical diagnostic wax-up 445 is manufactured from the digital diagnostic wax-up 441 using direct digital manufacture techniques, such as milling or 3D printing. The molding-shell 446 can be manufactured by arranging a molding-shell material at the manufactured diagnostic wax-up 445 and allowing the molding-shell material to harden as illustrated in FIG. 4C. The surface of the manufactured diagnostic wax-up is shaped according to the target shape of the restored teeth, such that the inner surface of the manufactured molding-shell also is shaped according to the target shape of the restored teeth.

Figure 4D:
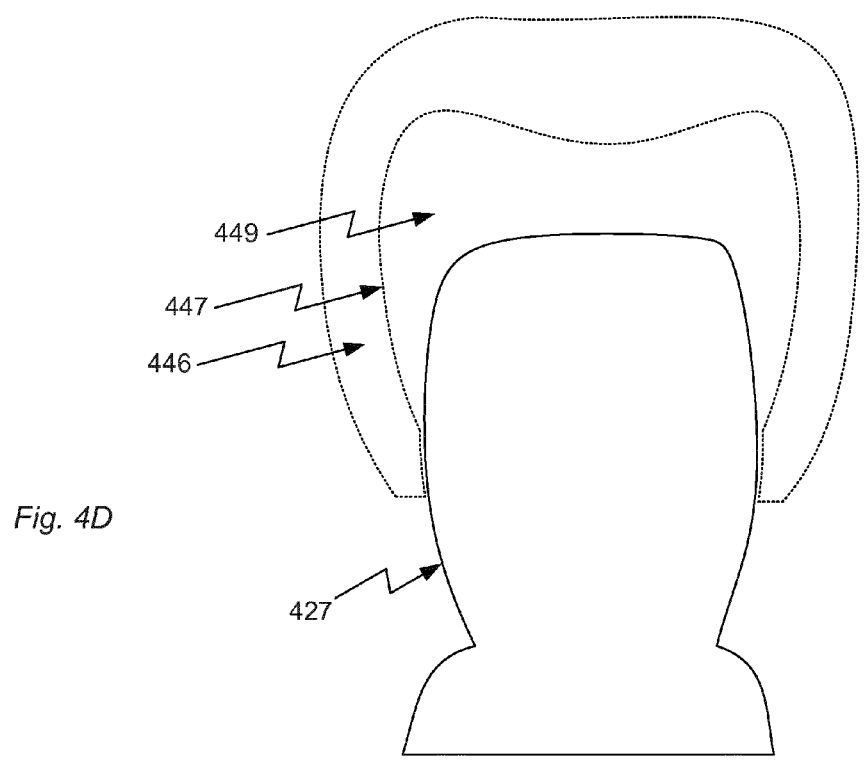

The manufactured molding-shell 446 can be arranged at the patient's existing teeth 427 such that the inner surface 447 of the molding-shell and the surface of the existing teeth enclose a volume 449 as illustrated in FIG. 4D. This enclosed volume is shaped according to the planned shape of the dental restoration such the dental restoration can be formed by filling the enclosed volume 449 with a dental material, such as e.g. wax, ceramics or an acrylic material, and allowing the dental material to harden.

FIG. 5 illustrates additional features of a digital diagnostic wax-up which provide advantageous functions of a manufactured molding-shell.

Figure 5A:
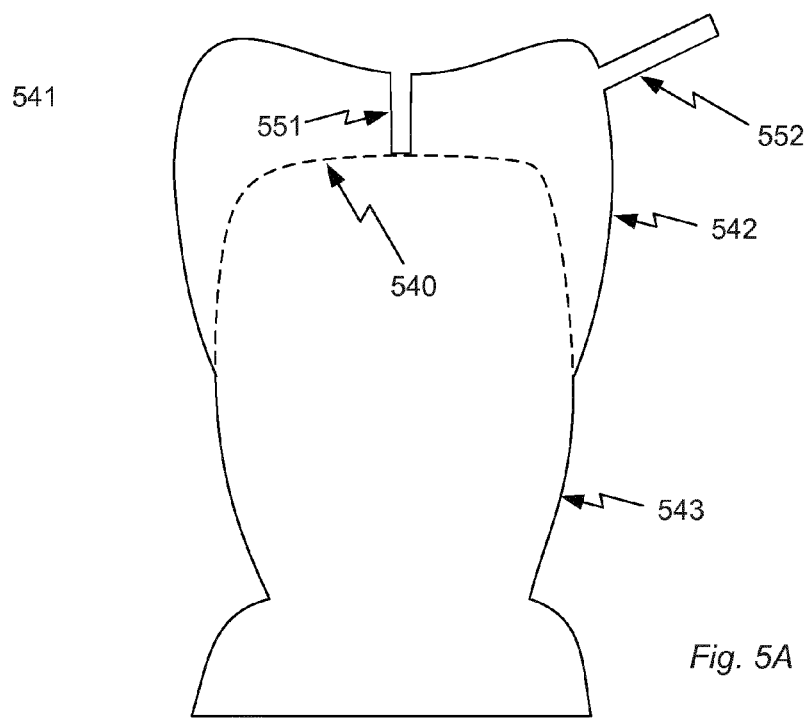
FIGS. 5A-5E illustrate additional features of a digital diagnostic wax-up which provide advantageous functions of a manufactured molding-shell.

FIG. 5A shows a digital design in the form of a diagnostic wax-up 541 with the first portion 542 shaped according to a digital teeth anatomy and a second portion second portion 543 shaped according to a tooth part of the digital 3D representation. Here a hole 551 is defined in the first portion 542 of the digital diagnostic wax-up 541, where the hole extends from the surface of the digital diagnostic wax-up to the tooth part of the digital 3D representation 540 (dotted line). The hole can be defined by a Boolean subtraction of a corresponding structure, such as a cylinder formed CAD model arranged such that it contacts the tooth part in the center of its occlusal surface.

Further a protrusion 552 is defined on the first portion 542 of the digital diagnostic wax-up 541. The protrusion can be defined by a Boolean addition of the corresponding structure, such as a cylinder formed CAD model. The length of the protrusion must be larger than the expected thickness of the molding-shell.

Figure 5B:
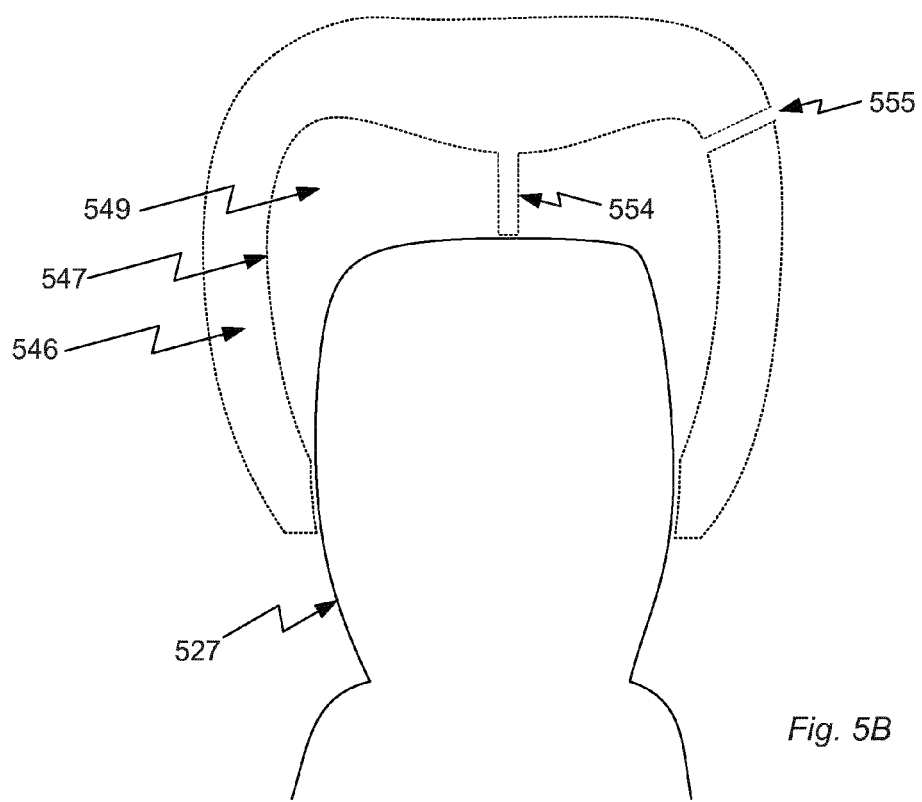

Similar to what was described in relation to FIG. 4C a physical diagnostic wax-up can be manufactured from the digital diagnostic wax-up and the molding-shell can then be manufactured by arranging a molding-shell material at the manufactured diagnostic wax-up and allowing the molding-shell material to harden. The additional features 551, 552 on the digital diagnostic wax-up influence the shape of the manufactured molding-shell. When the molding-shell material is arranged at the manufactured diagnostic wax-up the material will be introduced into the hole and form a support structure 554 while the protrusion will keep the material away and thus form a channel 555 in the manufactured molding-shell 546 (dotted line) as illustrated in FIG. 5B.

When the molding-shell is arranged at the patient's teeth the inner surface 547 of the molding-shell and the tooth surface still encloses a volume 549 for forming the dental restoration. The support structure 554 provides that the arrangement of the molding-shell 546 on the patient's existing teeth 527 is more precise and/or robust. The channel 555 provides an inlet/outlet for the dental material used for the dental restoration. In some cases the molding-shell is arranged at the teeth 527 and the dental material is injected into the enclosed volume 549 through the channel 555. In other cases the molding-shell is 546 is filled with the dental material prior to being arranged at the teeth 527. In such cases the channel 555 can act as an outlet of excess dental material.

Figure 5C:
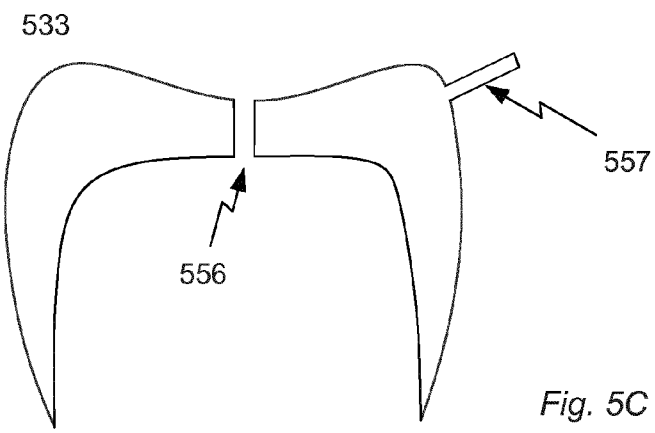
Figure 5D:
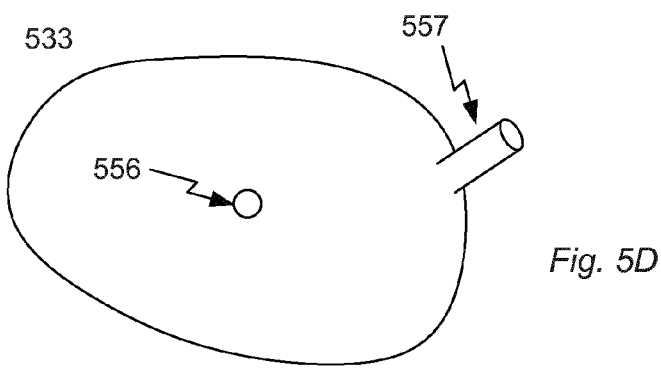

When the dental material has hardened, the molding-shell is removed. When the shell has a support structure and/or channel a slight post-processing is required. As illustrated in FIGS. 5C (side-view of dental restoration) and 5D (top-view of dental restoration) the support structure 554 will introduce a hole 556 in the formed dental restoration 533 and the (dental material filled) channel 555 will introduce a protrusion 557 on the surface. The hole 556 can easily be filled with e.g. the same dental material used to form the dental restoration while the protrusion 557 can be grinded/polished down such that the formed dental restoration has a smooth outer surface.

Figure 5E:
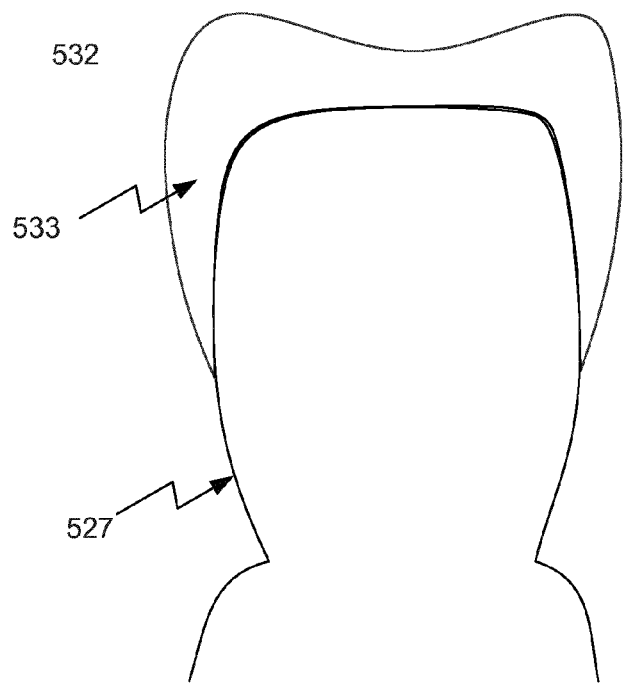

FIG. 5E shows the dental restoration 533 seated at the worn tooth 527 to form the restored tooth 532. In this example the dental restoration is a table-top restoration for raising the patient's bite but a similar work can be applied for manufacturing molding-shells for crowns, bridges, minimum-preparation veneers and other types of dental restorations, and equivalently the same types of dental restorations can be manufactured using these molding-shells.

FIG. 6 shows a schematic of a case where the digital design is a digital molding-shell design.

The digital teeth anatomies 639 are arranged in relation to the digital 3D representation 640 of the patient's existing teeth according to the preferred relative arrangement. In the illustrated example, the molding-shell is for forming a table-top dental restoration and the surface of the digital teeth anatomies is located such that the table-top restoration raises the patient's bite. The digital teeth anatomies and the digital 3D representation can be arranged relative to each other by expressing the digital teeth anatomies in the same coordinate system as the digital 3D representation and then move one relative to the other.

The digital teeth anatomies 639 can be obtained from a library of template teeth based on the dentist's preference while the digital 3D representation 640 can be obtained by different means such as by intra-oral scanning of the patient's teeth using the TRIOS intra-oral scanner by 3shape A/S.

A line of contact 638 between the digital teeth anatomies and the digital 3D representation is derived using a computer implemented algorithm configured for detecting surface-surface intersections. The digital teeth anatomies 639, the digital 3D representation 640, and the line of contact 638 can be visualized to the operator in a user interface displayed on e.g. a computer screen. In this user interface, the digital teeth anatomies 639 and the digital 3D representation 640 can be moved relative to each other using e.g. a computer mouse.

Figure 6A:
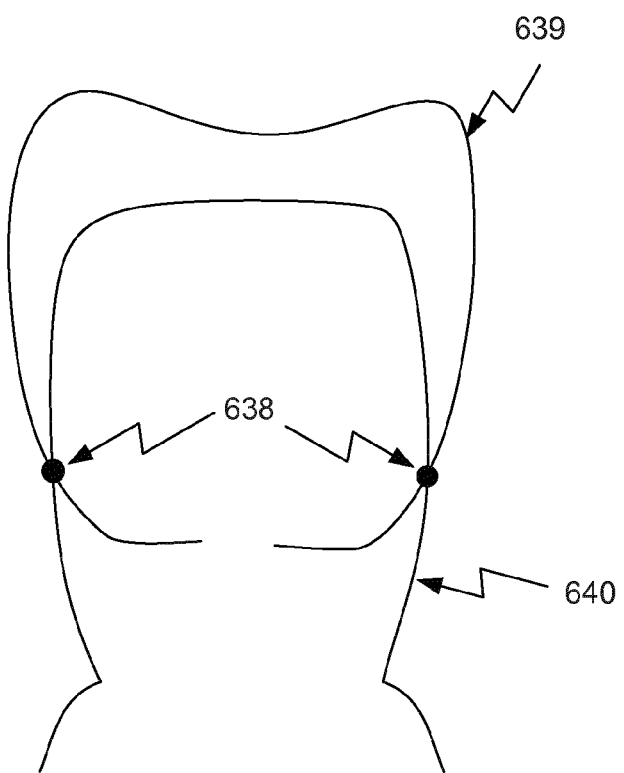
FIGS. 6A-6D show a schematic of a case where the digital design is a digital molding-shell design.
Figure 6B:
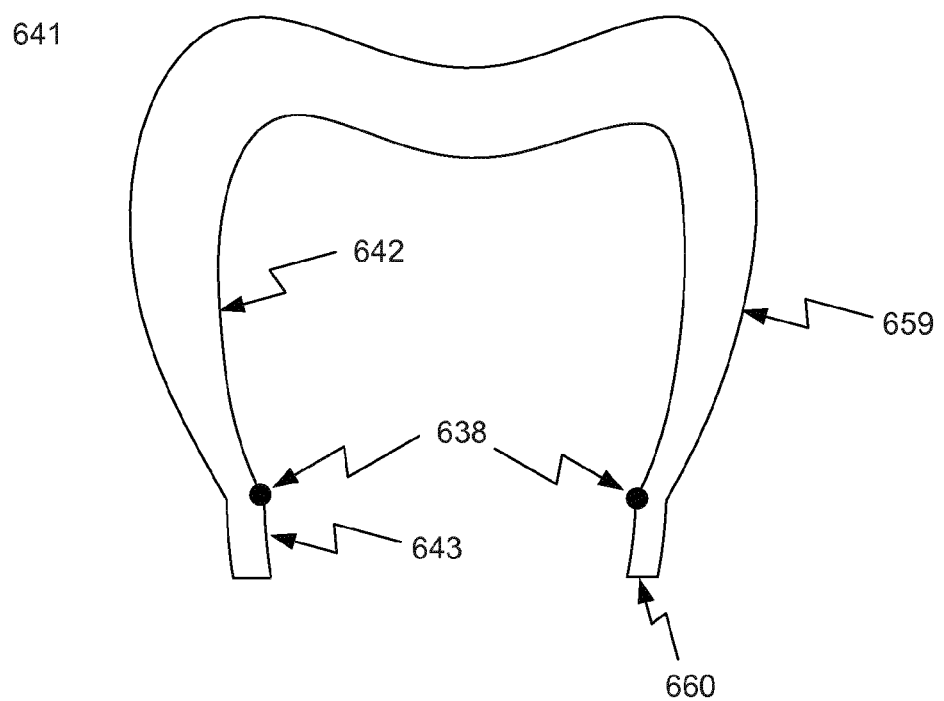

FIG. 6B shows a schematic of the generated digital molding-shell design 641.

When the line of contact 638 is found, the first portion 642 of the digital molding-shell design 641 is derived from a section of the digital teeth anatomies 639 coronal to the line of contact while the second portion 643 is derived from a section of the digital 3D representation cervical to the line of contact. Together the first and second portions define an inner surface of the digital molding-shell design 641. An outer surface 659 of the digital molding-shell design can be created e.g. by copying, offsetting and stretching the inner surface of the digital molding-shell design using computer implemented algorithms known to the skilled person. A connecting surface 660 is then formed, e.g. by a looting procedure, where the connecting surface is shaped to bridge the inner and outer surface of the digital molding-shell design. The digital molding-shell design is then a solid digital structure which can be interpreted by CAM equipment such that the molding-shell can be manufactured directly from the digital molding-shell design.

Similar to the case described in FIG. 5 for a digital diagnostic wax-up, additional features can be added to the digital molding-shell design seen in FIG. 6B. A digital support structure can be added by a Boolean addition of e.g. a cylindrical structure to the digital molding-shell design and a channel can be defined by a Boolean subtraction of a corresponding digital structure.

The molding-shell can subsequently be manufactured directly from the digital molding-shell design by direct digital manufacture such as 3D printing or milling. The resulting molding-shell 646 (dotted line) is illustrated together with the patient's teeth 627 in FIG. 6C. A first portion 647*i* of the inner surface (corresponding to the first portion 642 of the digital design) of the molding-shell encloses the volume 649 for the dental restoration together with the tooth surface. A second portion 647*ii* of the inner molding-shell surface (corresponding to the second portion 643 of the digital design) contacts a section of the tooth surface to provide support for the molding-shell at the teeth. A slight undercut may be allowed to provide a stronger support of the molding-shell. The support structure 654 engages the teeth to provide better support for the molding-shell at the teeth. The channel 655 provides and inlet or outlet of dental material as described under FIG. 5.

Figure 6C:
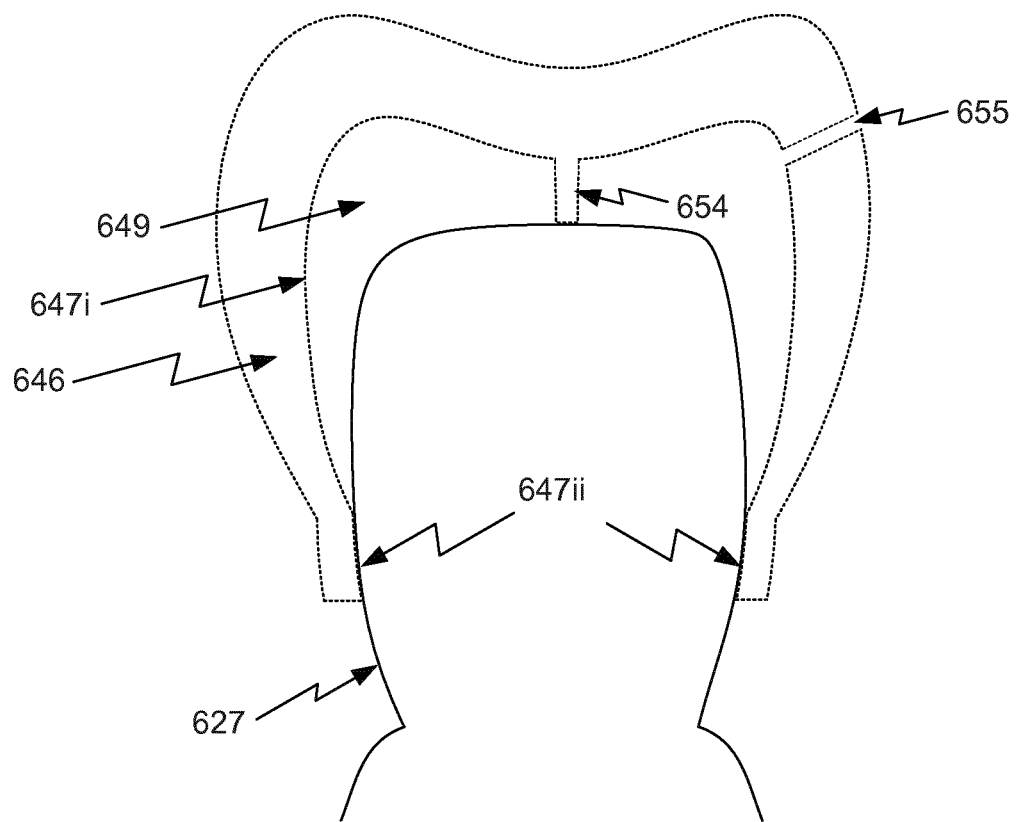
Figure 6D:
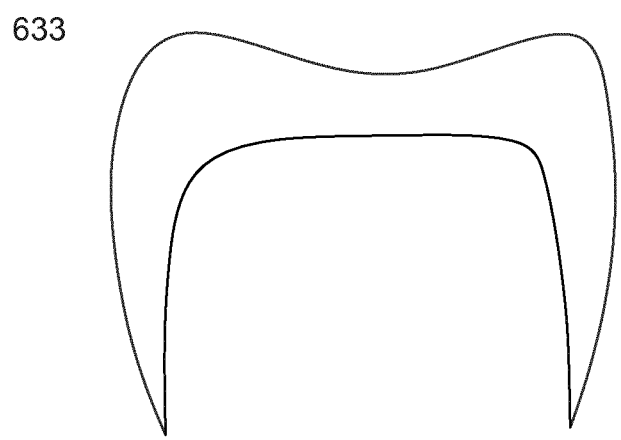

As also described in FIG. 5 the hole and protrusion of the dental restoration formed using the molding-shell seen in FIG. 6C can be filled/removed to provide a smooth outer surface of the formed dental restoration 633 as seen in FIG. 6D. This dental restoration is a table-top restoration configured for raising the patient's bite.

Figure 7:
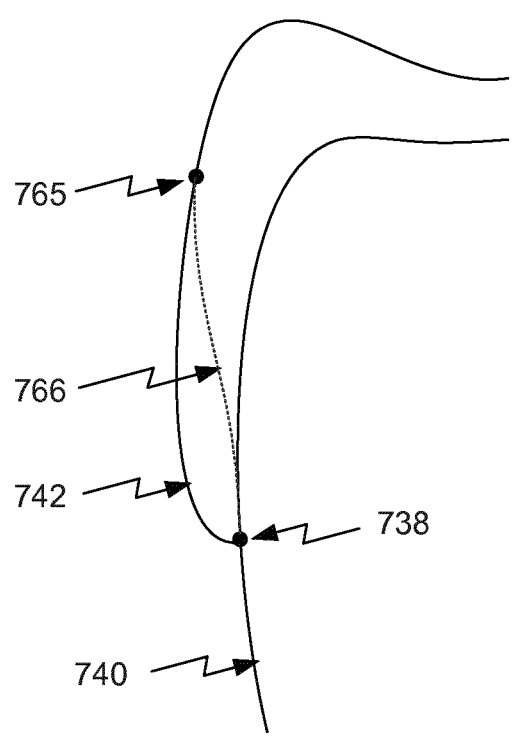
FIG. 7 illustrates curvature matching at the line of contact.

In order to provide an anatomical correct appearance of the restored tooth or teeth, it is often advantageous that the transition between the restoration and the visible part of the existing teeth is smooth. This can be achieved by e.g. curvature matching at the line of contact between the restoration and the existing teeth. FIG. 7 illustrates steps for providing a smooth transition.

The first portion 742 of the digital design is seen together with the digital 3D representation 740 of the corresponding tooth. The first portion is derived from digital teeth anatomies as described above in relation to e.g. FIGS. 5 and 6. As seen in the Figure, the transition between the first portion 742 and the digital 3D representation 740 is such that a visible kink will be present at the line of contact 738 if the dental restoration is formed from a molding-shell based on this digital design.

In the Figure, a curvature adjustment zone is limited by a boundary 765 and the line of contact 738. At the line of contact 738 the curvatures (of the first portion) of the digital design and of the digital 3D representation are determined and compared. If the curvatures differs more than a predetermined value, the first portion of the digital design is adapted to have a curvature similar to the curvature of the digital 3D representation (at the line of contact). The curvature adaptation is made smoothly such that the curvature adapted portion 766 of the first portion of the digital design gradually adapts to match the curvature of the digital 3D representation of the patient's teeth at the line of contact 738 and match the original shape of the digital design at the boundary 765.

Outside the boundary 765 of the curvature adjustment zone the digital design 742 is preferably not modified but maintains its shape. The boundary 765 of the curvature adjustment zone is identified either manually by marking a 3D spline on the digital design 742 or automatically by computer implemented algorithms e.g. based on a predefined distance from the line of contact and the difference in curvature of the digital design and the digital 3D representation at the line of contact. The boundary 765 can also be defined as the point where the digital design contacts the part of the digital 3D representation corresponding to the neighbor teeth.

When the molding-shell is manufactured based on the modified digital design, the enclosed volume will be such that the formed dental restoration will have a smooth transition to the tooth and thus that the dental restoration feels like a natural part of the tooth/teeth.

Figure 8:
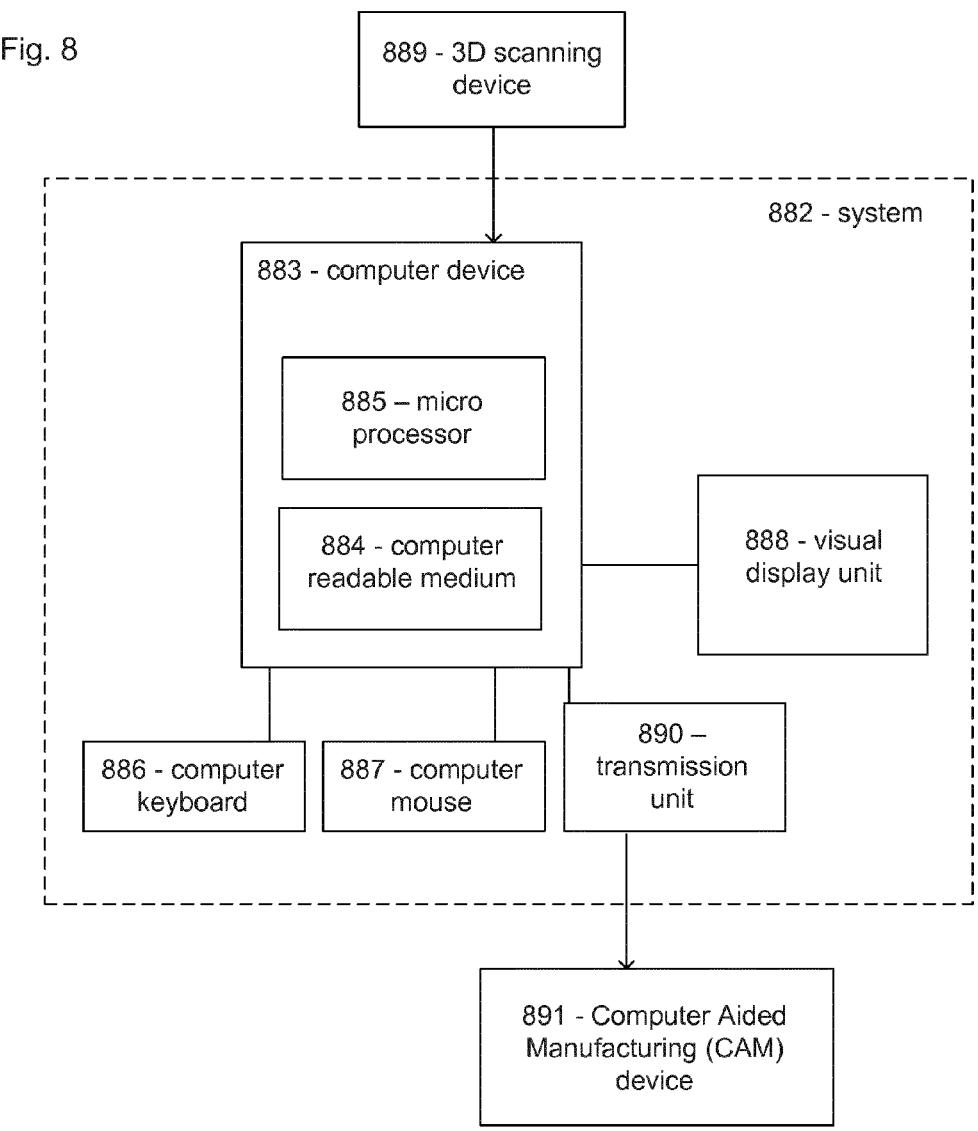
FIG. 8 shows a schematic of a system.

FIG. 8 shows a schematic of a system according to an embodiment. The system 882 comprises a computer device 883 comprising a computer readable medium 884 and an electronic data processing device in the form of a microprocessor 885. The system further comprises a visual display unit 888, a computer keyboard 886 and a computer mouse 887 for entering data and activating virtual buttons of a user interface visualized on the visual display unit 888. The visual display unit 888 can e.g. be a computer screen.

The computer device 883 is capable of obtaining at least a digital 3D representation of a part of the patient's teeth for which a dental restoration is to be formed. The digital 3D representation can be received from a 3D scanning device 889, such as the TRIOS intra-oral scanner manufactured by 3shape TRIOS A/S, or scan data from such a 3D scanning device can be received and such that the digital 3D representation of the patient's teeth is formed the based on these scan data. The received or formed digital 3D representation can be stored in the computer readable medium 884 and loaded to the microprocessor 885. The computer device 883 is further capable of obtaining at least one digital teeth anatomy which will be used for determining the shape of the outer surface of the dental restoration. The obtained digital 3D representation and digital teeth anatomies can be stored in the computer readable medium 884 and loaded to the microprocessor 885. The system 882 is configured for allowing an operator to arrange the digital 3D representation and digital teeth anatomies relative to each other in a manner that reflects the preferred relative arrangement of the outer surface of the manufactured dental restoration relative to the patient's teeth. For a table-top restoration the preferred relative arrangement is that which provides the desired raise of the patient's bite, i.e. where the dental restoration raises the occlusal surface of the teeth. For a crown restoration the preferred relative arrangement is that which provides the target shape of the restored tooth. This can be realized by displaying the digital 3D representation and digital teeth anatomies in a user interface depicted on the visual display unit 888 and the operator can adjust their relative arrangement using e.g. the computer mouse 887 or the computer keyboard 886. The computer device 883 is configured for executing algorithms for generating the digital design for use in the manufacture of the molding-shell. The algorithms can be based on a Boolean addition of solid digital structures and/or on detecting an intersection between the digital 3D representation and the digital teeth anatomies as described above in relation to FIGS. 1, and 4 to 6.

When performing different steps of a method, such as when arranging the digital 3D representation of the teeth and the digital teeth anatomies in relation to each other, one or more options can be presented to the operator, such as which digital teeth anatomies to select or whether he wishes to create the digital design in the form of a digital diagnostic wax-up or as a digital molding-shell design. The options can be presented in a user interface visualized on the visual display unit 888.

The system can have a unit 890 for transmitting the created a digital design to e.g. a computer aided manufacturing (CAM) device 891 for manufacturing e.g. the molding-shell or to another computer system e.g. located at a milling center where the molding-shells or diagnostic wax-ups are manufactured. The unit for transmitting can be a wired or a wireless connection.

The 3D scanning of the patient's teeth using the 3D scanning device 889 can be performed at a dentist office while the creating of the digital design is performed at a dental laboratory. In such cases the digital 3D representation of the patient's teeth can be provided to the dental laboratory e.g. via an internet connection.

Figure 9:
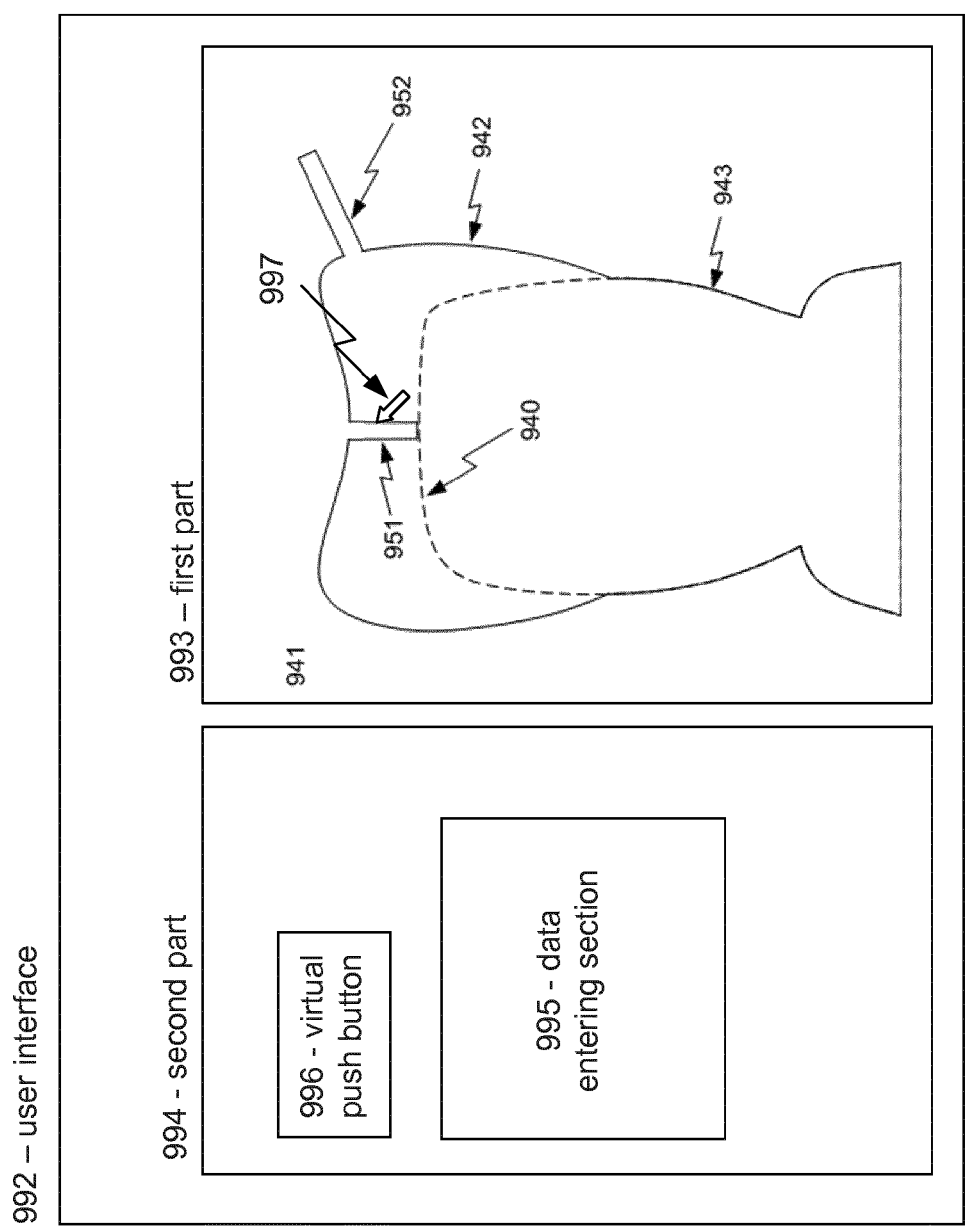
FIG. 9 shows a schematic of a user interface.

FIG. 9 shows a schematic of a user interface according to an embodiment.

In this example, the digital design is in the form of a diagnostic wax-up 941 with the first portion 942 shaped according to a digital teeth anatomy and a second portion second portion 943 shaped according to a tooth part of the digital 3D representation. In FIG. 9 a first part 993 of the user interface 992 is seen in which a cross section of a generated digital diagnostic wax-up 941 and a part of a digital 3D representation 940 of the teeth are illustrated. A hole 951 is defined in the first portion 942 of the digital diagnostic wax-up 941, where the hole extends from the surface of the digital diagnostic wax-up 941 to the tooth part of the digital 3D representation 940 (dotted line).

The position of the hole 951 relative to the digital diagnostic wax-up 941 and to the digital 3D representation 940 can be adjusted using a digital tool 997. The digital tool can be configured for grabbing e.g. the digital structure expressing the shape and size of the hole (e.g. a CAD model of a cylindrical structure) and moving it in the user interface using e.g. a computer mouse. Alternatively, the operator can use the digital tool to identify a point on the digital diagnostic wax-up 941 or on the tooth part of the digital 3D representation 940 from where the hole should extend to the other. Thereafter a computer implemented algorithm can then generate the hole in the digital diagnostic wax-up.

Further a protrusion 952 is defined on the first portion 942 of the digital diagnostic wax-up 941. The protrusion can be defined by a Boolean addition of the corresponding structure, such as a cylinder formed CAD model. The position and orientation of the protrusion can also be manipulated using the digital tool 997.

The second part 994 of the user interface comprises a data entering section 995 for entering data relating to e.g. whether the digital design is a digital diagnostic wax-up or a digital molding-shell design and how the digital design is to be generated. A virtual push button 996 is configured for creating the digital design taking into account the data entered in the data entering section 995.

The user interface can be visualized on a visual display unit, such as a computer screen being part of a system configured for implementing the disclosed method.

FIG. 10 illustrates a digital design for the molding-shell based on a digital restoration design.

Figure 10A:
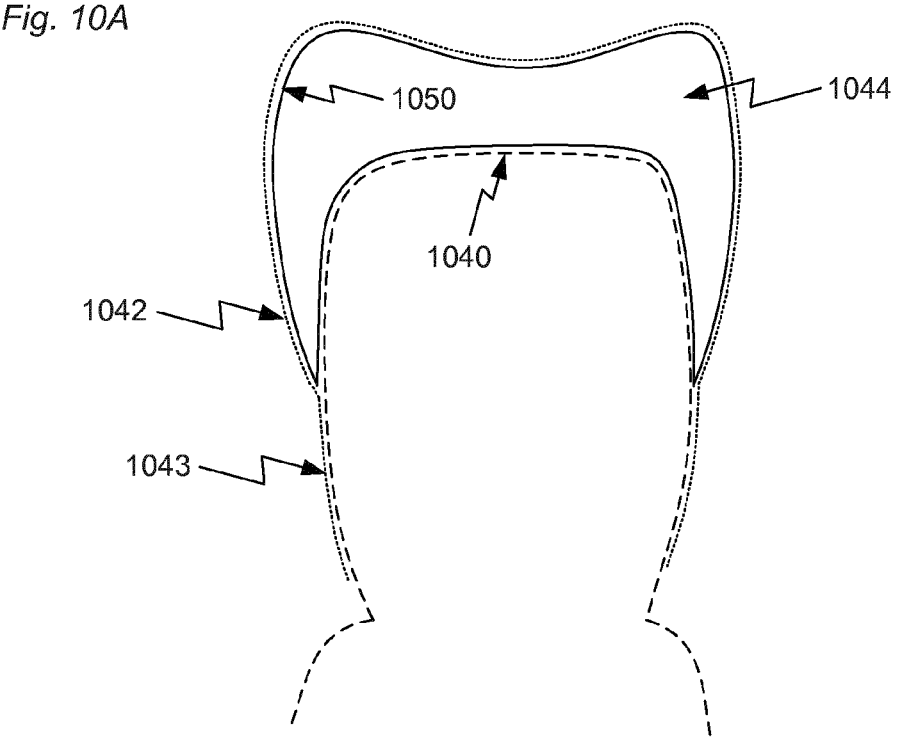
FIGS. 10A-10B illustrate a digital design for the molding-shell based on a digital restoration design.

When a digital restoration design 1044 expressing the desired shape of the dental restoration has been created at the digital 3D representation of the patient's teeth 1040, the outer surface 1050 of the digital restoration design can be used as the first portion 1042 of the digital design while part of the digital 3D representation 1040 can be used as the second portion 1043 as illustrated in FIG. 10A. The first portion 1042 can be created by copying the part of the outer surface of the digital restoration design and inverting the copied surface. The part of the digital 3D representation 1040 which is used for creating the second portion 1043 can be selected by an operator e.g. by defining a boundary of the used part in a visualization of the digital 3D representation in a user interface.

Figure 10B:
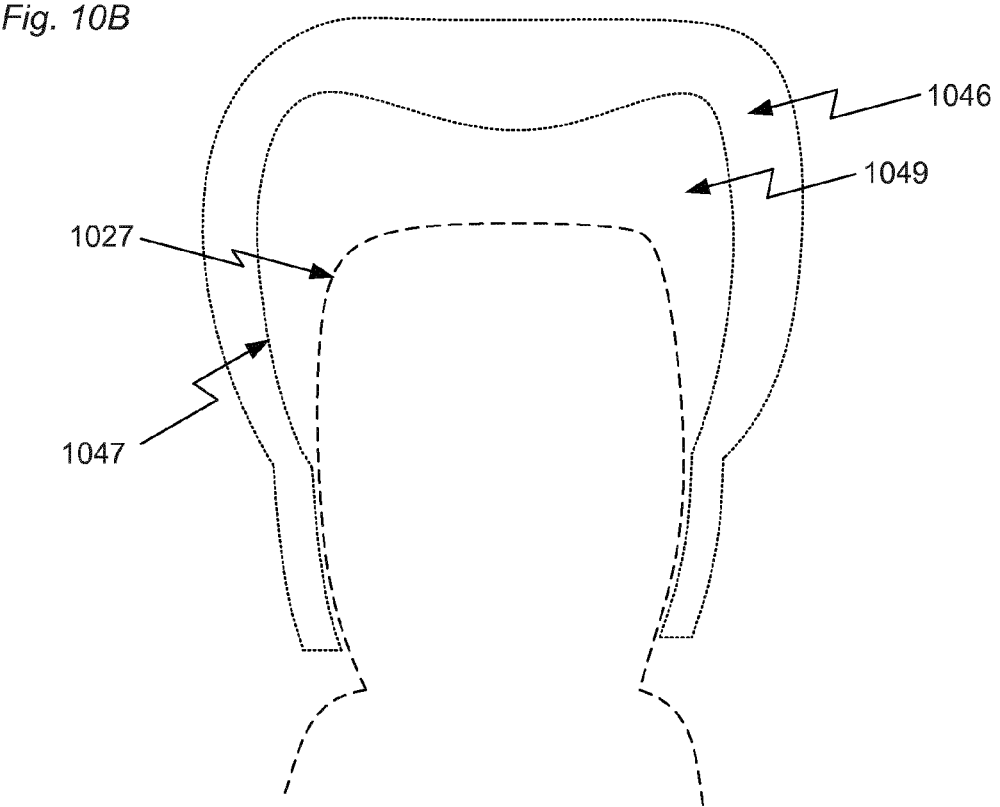

The molding-shell 1046 can be manufactured using either the diagnostic wax-up approach or the creating of a digital molding-shell design both described above. When arranged at the patient's exiting teeth 1027 the inner surface 1047 of the manufactured molding-shell 1046 and the surface of the teeth together define the volume for the dental material used for the manufacture of the dental restoration as illustrated in FIG. 10B.

Additional features such as the channel and support structures described above can also be provided using the approach described in relation to this Figure.

Although some embodiments have been described and shown in detail, the invention is not restricted to them, but may also be embodied in other ways within the scope of the subject matter defined in the following claims. In particular, it is to be understood that other embodiments may be utilized and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions.

The instructions may be program code means loaded in a memory, such as a RAM, from a storage medium or from another computer via a computer network. Alternatively, the described features may be implemented by hardwired circuitry instead of software or in combination with software.

SELECTED FIGURE REFERENCE NUMBERS

In the Figures the reference numbers are provided in the format according to XYY where "X" is a Figure number indicator showing in which Figure the reference is used and YY is the item number indicator according to the following list.

Patient's teeth 20
Tooth intersected by cross sectional line 21
Existing teeth 27
Occlusal table of existing teeth 28
Original shape of the teeth 29
Original occlusal table of teeth 30
Restored tooth/teeth 32
Dental restoration 33
Inner surface of restoration 35
Outer surface of restoration 36
Line of contact 38
Digital tooth anatomy/digital teeth anatomies 39
Digital 3D representation of existing teeth 40
Digital design/Digital diagnostic wax-up/digital molding-shell design 41
First portion of digital design 42
Second portion of digital design 43
Digital restoration design 44
Manufactured diagnostic wax-up 45
Manufactured molding-shell 46
Inner surface of molding-shell 47

Enclosed volume 49
Outer surface of digital restoration design 50
Hole in digital diagnostic wax-up 51
Protrusion on digital diagnostic wax-up 52
Support structure on formed molding-shell 54
Channel in formed molding-shell 55
Hole in dental restoration 56
Protrusion on dental restoration 57
Outer surface of digital design 59
Connecting surface 60
Boundary of curvature adjustment zone 65
Curvature adjusted portion 66
System 82
Computer device 83
Computer readable medium 84
Microprocessor 85
Computer keyboard 86
Computer mouse 87
Visual display unit 88
3D scanning device 89
Transmission unit 90
Computer aided manufacturing (CAM) device 91
User interface 92
First part of user interface 93
Second part of user interface 94
Data entering section 95
Virtual push button 96
Digital tool 97

The invention claimed is:

1. A method for generating a digital design for use in the manufacture of a molding-shell for a patient's tooth, where the molding-shell and the tooth together enclose a volume for forming a dental restoration, where the method comprises:
   obtaining a digital 3D representation of the patient's tooth, said digital 3D representation comprising a tooth part relating to one or more teeth for which the dental restoration is formed;
   obtaining a set of one or more digital teeth anatomies;
   arranging the set of one or more digital teeth anatomies and the digital 3D representation according to a preferred relative arrangement; and
   generating the digital design where a first portion of the digital design is derived from the one or more digital teeth anatomies and a second portion of the digital design is derived from the tooth part of the digital 3D representation.

2. The method according to claim 1, wherein the digital design comprises a digital molding-shell design and the first and second portions define an inner shell surface of the digital molding-shell design.

3. The method according to claim 2, wherein generating the digital design comprises creating an outer shell surface of the digital molding-shell design.

4. The method according to claim 2, wherein the method comprises adding one or more digital support structures to the digital molding-shell design where the digital support structures extend from the inner shell surface to the tooth part of the digital 3D representation.

5. The method according to claim 2, wherein the method comprises defining a channel in the digital molding-shell design, where the channel extends from the inner shell surface to the outer shell surface.

6. The method according to claim 1, wherein generating the digital design comprises a Boolean addition of the digital 3D representation and the set of one or more digital teeth anatomies.

7. The method according to claim 1, wherein the method comprises determining a line of contact for the digital 3D representation and the set of one or more digital teeth anatomies, wherein the line of contact is derived from an intersection of the digital 3D representation and the one or more digital teeth anatomies, and wherein the first portion is derived from a section of the set of one or more digital teeth anatomies coronal to the line of contact and the second portion is derived from a section of the digital 3D representation cervical to the line of contact.

8. The method according to claim 1, wherein the method comprises determining a planned thickness of the dental restoration as the distance from the digital 3D representation of the patient's teeth to the digital design or to the one or more digital teeth anatomies, and examining the planned thickness with respect to one or more minimum thickness criteria to identify any problematic regions.

9. The method according to claim 1, wherein the method comprises creating a digital restoration design for the dental restoration, where the digital restoration design expresses the planned shape of the dental restoration.

10. The method according to claim 1, wherein the digital design comprises a third portion derived from a portion of the digital 3D representation corresponding to neighboring teeth and/or soft tissue.

11. The method according to claim 1, wherein the digital design comprises a digital diagnostic wax-up.

12. The method according to claim 11, wherein the method comprises defining one or more holes in the digital diagnostic wax-up, where the holes extend from the surface of the digital diagnostic wax-up to the tooth part of the digital 3D representation.

13. The method according to claim 11, wherein the method comprises defining a protrusion on the digital diagnostic wax-up.

14. A method for manufacturing a molding-shell for a patient's tooth, where the molding-shell and the tooth together enclose a volume for forming a dental restoration, where the method comprises:
   generating a digital design using a method according to claim 1, and
   manufacturing a physical copy of the digital design using direct digital manufacture equipment.

15. The method according to claim 14, wherein the digital design comprises a digital diagnostic wax-up such that the manufactured physical copy comprises a physical diagnostic wax-up, and the method comprises arranging a molding-shell material at the manufactured physical diagnostic wax-up such that the molding-shell is manufactured with an inner surface shape defined by the physical diagnostic wax-up.

16. The method according to claim 14, wherein the digital design comprises a digital molding-shell design such that the physical copy manufactured from the digital design comprises the molding-shell.

17. The method according to claim 1, wherein the molding shell and the tooth together define an entirety of the volume for forming a dental restoration.

18. The method according to claim 1, wherein the digital design comprises an outer surface of the dental restoration where a first portion of the digital design is derived from the one or more digital teeth anatomies and a second portion of the digital design is derived from the tooth part of the digital 3D representation.

19. The method according to claim 1, wherein a first portion of an inner surface of the molding-shell defines part of a boundary of the enclosed volume such that a portion of the outer surface of the formed restoration is shaped according to this first portion.

20. The method according to claim 19, wherein a second portion of the inner surface of the molding-shell is configured to engage the patient's tooth to provide support for the molding-shell at the tooth.

21. A system for designing a digital design for manufacturing a molding-shell for a patient's tooth, where the molding-shell and the tooth together enclose a volume for forming a dental restoration, wherein the system comprises:
- a computer device comprising a non-transistory computer readable medium and an electronic data processing device, where said computer device is capable of obtaining a set of one or more digital teeth anatomies and a digital 3D representation of the patient's teeth, where said digital 3D representation comprises a tooth part relating to one or more teeth for which the dental restoration is formed;
- a visual display unit for displaying the one or more digital teeth anatomies and the digital 3D representation of the patient's tooth; and
- digital tools allowing an operator to arrange the set of one or more digital teeth anatomies and the digital 3D representation according to a preferred relative arrangement;

where the computer readable medium comprises computer code which when executed on the electronic data processing device generates the digital design, where a first portion of the digital design is derived from the one or more digital teeth anatomies and a second portion of the digital design is derived from the tooth part of the digital 3D representation.

22. The system according to claim 21, wherein the molding shell and the tooth together define an entirety of the volume for forming a dental restoration.

23. The system according to claim 21, wherein the digital design comprises an outer surface of the dental restoration where a first portion of the digital design is derived from the one or more digital teeth anatomies and a second portion of the digital design is derived from the tooth part of the digital 3D representation.

24. The system according to claim 21, wherein a first portion of an inner surface of the molding-shell defines part of a boundary of the enclosed volume such that a portion of the outer surface of the formed restoration is shaped according to this first portion.

25. The system according to claim 24, wherein a second portion of the inner surface of the molding-shell is configured to engage the patient's tooth to provide support for the molding-shell at the tooth.

* * * * *